US008529880B2

(12) United States Patent
Adhikari et al.

(10) Patent No.: US 8,529,880 B2
(45) Date of Patent: *Sep. 10, 2013

(54) BIODEGRADABLE POLYURETHANE/UREA COMPOSITIONS

(71) Applicants: Raju Adhikari, Wheelers Hill (AU); Pathiraja Arachchillage Gunatillake, Mulgrave (AU)

(72) Inventors: Raju Adhikari, Wheelers Hill (AU); Pathiraja Arachchillage Gunatillake, Mulgrave (AU)

(73) Assignee: Polynovo Biomaterials Pty Limited, Clayton, Victoria (AU)

( * ) Notice: Subject to any disclaimer, the term of this patent is extended or adjusted under 35 U.S.C. 154(b) by 0 days.

This patent is subject to a terminal disclaimer.

(21) Appl. No.: 13/665,531

(22) Filed: Oct. 31, 2012

(65) Prior Publication Data

US 2013/0121969 A1    May 16, 2013

Related U.S. Application Data

(63) Continuation of application No. 10/520,414, filed as application No. PCT/AU03/00935 on Jul. 23, 2003, now Pat. No. 8,343,472.

(30) Foreign Application Priority Data

Jul. 23, 2002 (AU) .............................. 2002950340

(51) Int. Cl.
    *A61K 31/74* (2006.01)
(52) U.S. Cl.
    USPC ...................................... 424/78.08
(58) Field of Classification Search
    None
    See application file for complete search history.

(56) References Cited

U.S. PATENT DOCUMENTS

| 3,281,378 A | 10/1966 | Garber et al. |
| 4,192,827 A | 3/1980 | Mueller et al. |
| 4,273,690 A | 6/1981 | Walus |
| 4,284,506 A | 8/1981 | Tetenbaum et al. |
| 4,293,679 A | 10/1981 | Cogliano |
| 4,412,033 A | 10/1983 | LaBelle et al. |
| 4,908,406 A | 3/1990 | Mulhaupt et al. |
| 5,041,516 A | 8/1991 | Frechet et al. |
| 5,578,662 A | 11/1996 | Bennett et al. |
| 5,886,127 A | 3/1999 | Newkome et al. |
| 5,981,684 A | 11/1999 | Bruchmann et al. |
| 6,150,438 A | 11/2000 | Shiraishi et al. |
| 6,221,997 B1 | 4/2001 | Woodhouse et al. |
| 6,376,637 B1 | 4/2002 | Bruchmann et al. |
| 6,376,742 B1 | 4/2002 | Zdrahala et al. |
| 6,388,047 B1 | 5/2002 | Won et al. |

(Continued)

FOREIGN PATENT DOCUMENTS

| EP | 837084 A3 | 12/1998 |
| WO | WO-0012579 A1 | 3/2000 |
| WO | WO-0119887 A1 | 3/2001 |
| WO | WO-0210247 A1 | 2/2002 |

*Primary Examiner* — Paul Dickinson
(74) *Attorney, Agent, or Firm* — Novak Druce Connelly Bove + Quigg LLP

(57) ABSTRACT

The present invention relates to biocompatible, biodegradable polyurethane/urea polymeric compositions that are capable of in-vivo curing with low heat generation to form materials suitable for use in scaffolds in tissue engineering applications such as bone and cartilage repair. The polymers are desirably flowable and injectable and can support living biological components to aid in the healing process. They may be cured ex-vivo for invasive surgical repair methods, or alternatively utilized for relatively non-invasive surgical repair methods such as by arthroscope. The invention also relates to prepolymers useful in the preparation of the polymeric compositions, and to methods of treatment of damaged tissue using the polymers of the invention.

22 Claims, 18 Drawing Sheets

Effect of water, lactose, and triethylene glycol (TEG) on compressive strength

(56) References Cited

U.S. PATENT DOCUMENTS

| | | |
|---|---|---|
| 6,555,645 B1 | 4/2003 | Ikeda et al. |
| 2001/0005738 A1 | 6/2001 | Bruchmann et al. |
| 2004/0097684 A1 | 5/2004 | Bruchmann et al. |
| 2005/0197422 A1 | 9/2005 | Mayadunne et al. |
| 2009/0081270 A9 | 3/2009 | Moore et al. |
| 2009/0099600 A1 | 4/2009 | Moore et al. |

Effect of water, lactose, and triethylene glycol (TEG) on compressive strength

Effect of different degradable cross-linker structure on average porosity

PCLT-C = polycaprolactone triol, PCLT-HA = (hydroxyapatite), PCLT-SA-PW = silica powder, PCLT-SA-Pt = silica powder, PCLT-PLGA = poly(glycolic and lactic acid) copolymer

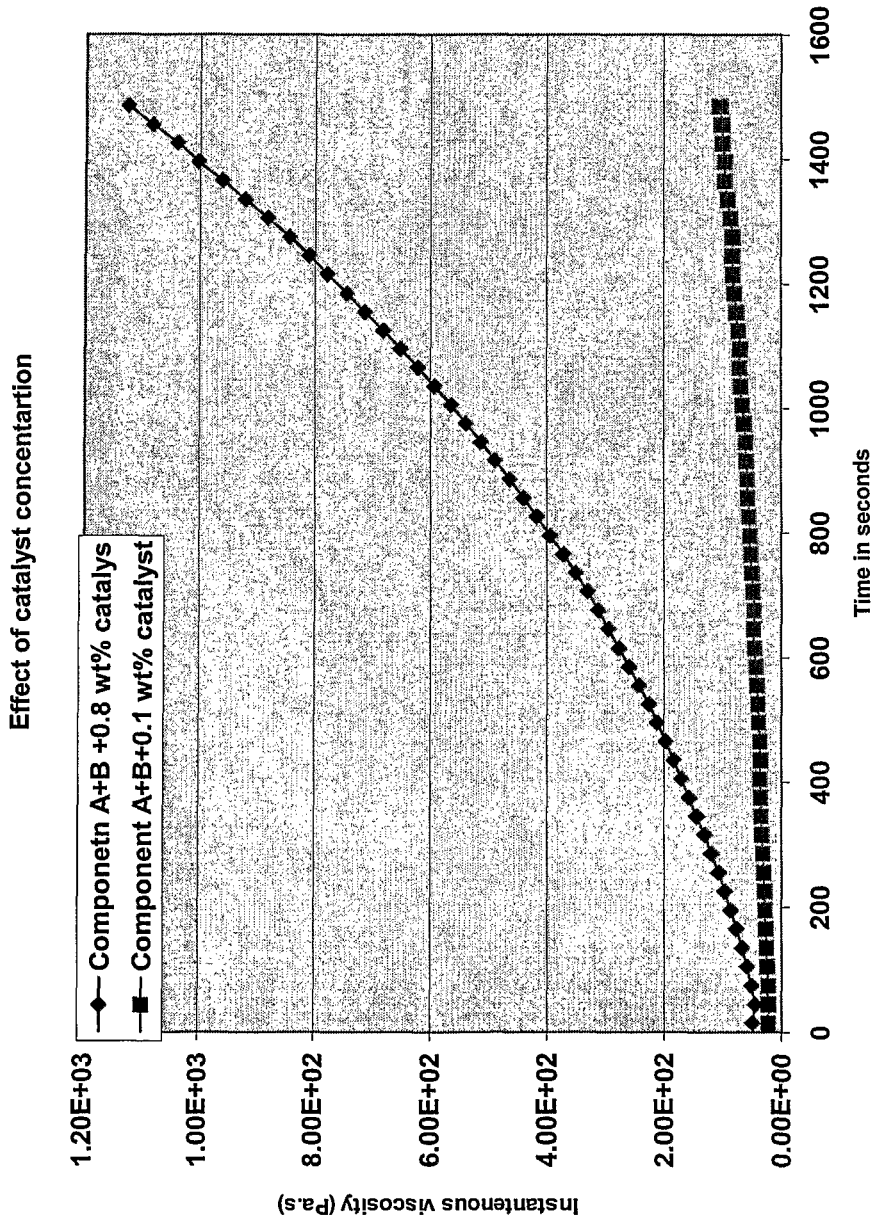
Figure 12: Change in polymer viscosity with curing time at 23°C

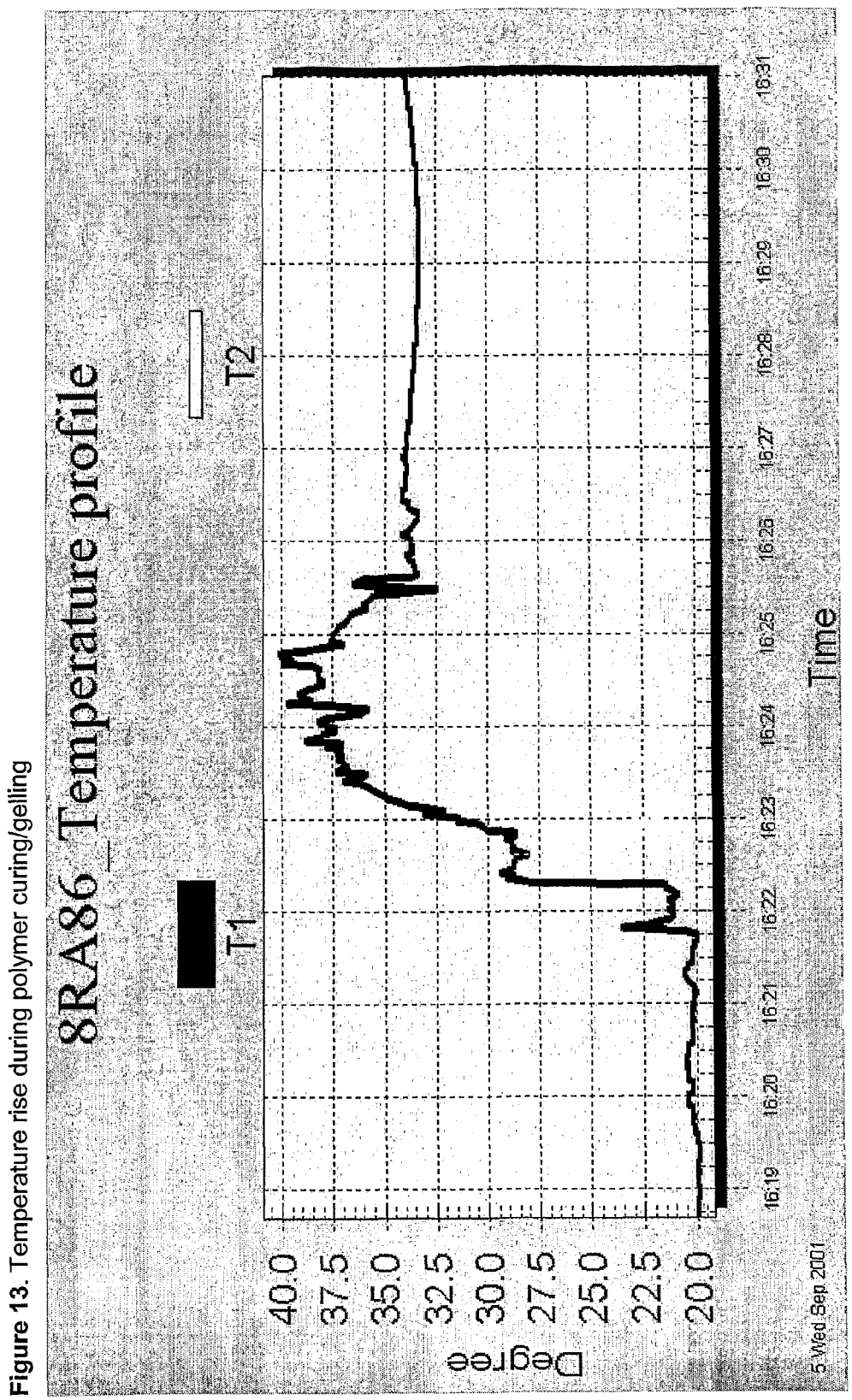
Figure 13. Temperature rise during polymer curing/gelling

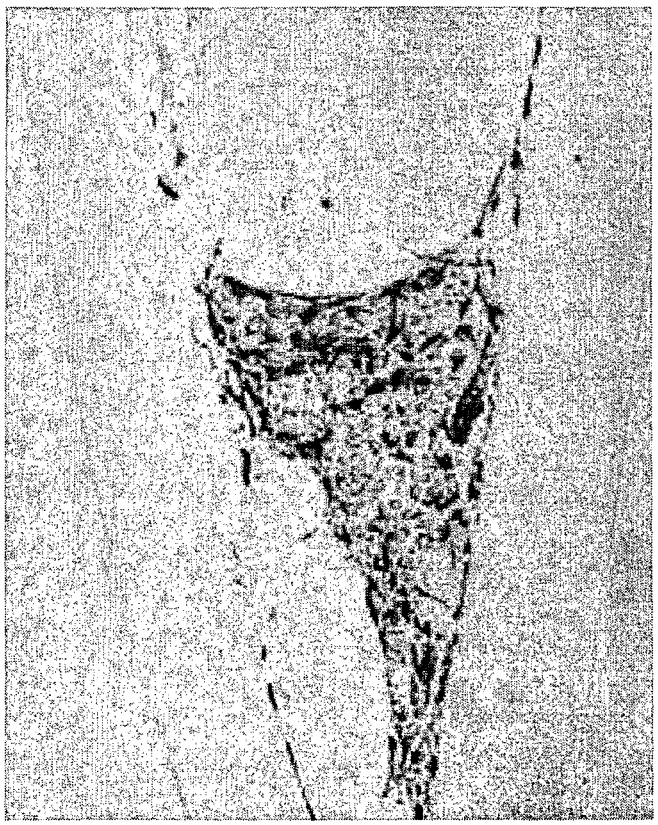
Figure 14. Haematoxylin & Eosin staining of a 6 week culture showing cluster of viable stem cells (purple) and new matrix (pink) within hollow fibres (transparent) within the polymer scaffold.

Figure 15. 6 week culture of human mesenchymal stem cells grown in hollow fibres within the polymer scaffold supplemented with differentiation medium to promote osteoblast differentiation. Sample is stained with von Kossa to show bone mineralisation (brown/black staining).

Figure 16. Haematoxylin & Eosin staining of a 4 week culture showing cluster of viable chondrocytes within resorbed gelatin beads within the polymer scaffold.

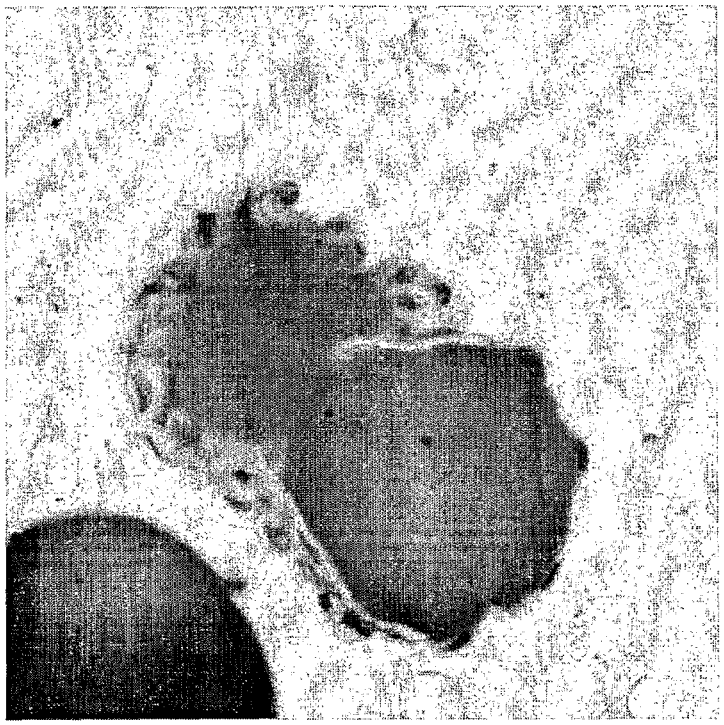
Figure 17. Alcian blue staining of a 9 week culture showing cluster of viable chondrocytes around gelatin beads within the polymer scaffold. Pink staining indicates cells and blue around cells indicates new glycosaminoglycan synthesis.

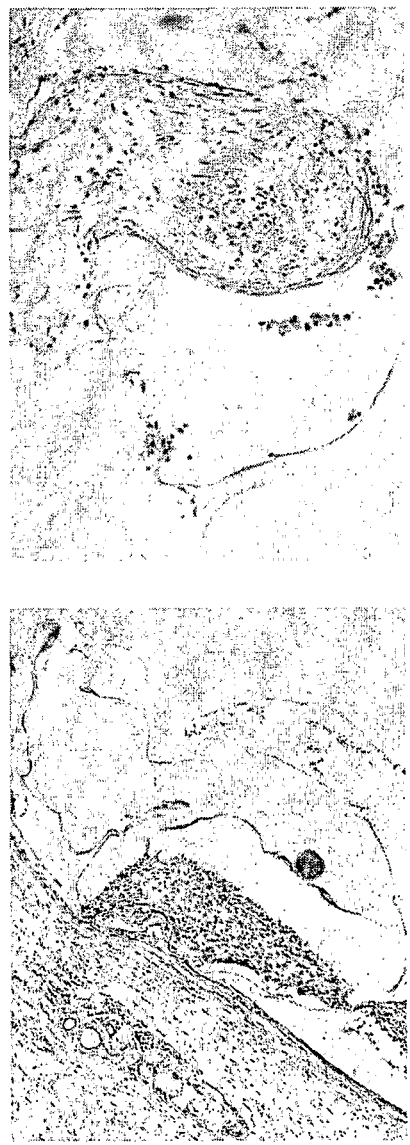
Figure 18: Micrographs showing cellular integration in to the polymer structure after 2-month implantation in rats (a) Polymer implant sample # 1 (b) Polymer implant sample #2.

BIODEGRADABLE POLYURETHANE/UREA COMPOSITIONS

CROSS-REFERENCE TO RELATED APPLICATIONS

This application is a continuation of application Ser. No. 10/520,414 filed on Jan. 6, 2005. Application Ser. No. 10/520,414 is a National Phase of PCT/AU03/00935, filed Jul. 23, 2003, which claims priority to Australian Application No. 2002950340, filed on Jul. 23, 2002, the entire contents of which is hereby incorporated by reference.

FIELD OF THE INVENTION

The present invention relates to biocompatible, biodegradable polymeric compositions that are capable of in-vivo curing with low heat generation to form materials suitable for use in scaffolds in tissue engineering applications such as bone and cartilage repair. The polymers are desirably flowable and injectable and can support living biological components to aid in the healing process. They may be cured ex-vivo for invasive surgical repair methods, or alternatively utilized for relatively non-invasive surgical repair methods such as by arthroscope. The invention also relates to prepolymers useful in the preparation of the polymeric compositions, and to methods of treatment of damaged tissue using the polymers of the invention.

BACKGROUND

Biodegradable synthetic polymers offer a number of advantages over other materials in various biological applications including bone and cartilage repair. For example, in relation to the development of scaffolds in tissue engineering, the key advantages include the ability to tailor mechanical properties and degradation kinetics to suit various applications. Synthetic polymers are also attractive in tissue engineering applications because they can be fabricated into various shapes with desired pore morphologic features conducive to tissue in growth. Furthermore, polymers can be designed with chemical functional groups that can, for example, induce tissue in-growth, or be utilised to adapt the polymers to the application in question.

A vast majority of biodegradable polymers studied belong to the polyester family. Among these poly(α-hydroxy acids) such as poly(glycolic acid), poly(lactic acid) and a range of their copolymers have historically comprised the bulk of published material on biodegradable polyesters and has a long history of use as synthetic biodegradable materials[1-3] in a number of clinical applications. Among these applications, poly(glycolic acid), poly(lactic acid) and their copolymers, poly-p-dioxanone, and copolymers of trimethylene carbonate and glycolide have been the most widely used. The major applications include resorbable sutures, drug delivery systems and orthopedic fixation devices such as pins, rods and screws[4-5]. Among the families of synthetic polymers, the polyesters have been attractive for these applications because of their ease of degradation by hydrolysis of ester linkage, degradation products are resorbed through the metabolic pathways in some cases and the potential to tailor the structure to alter degradation rates.

The recent interest in finding tissue-engineered solutions to repair damaged tissues and organs due to injuries/diseases has made necessary the development of new degradable polymers that meet a number of demanding requirements. These requirements range from the ability of the polymer scaffold to provide mechanical support during tissue growth and gradually degrade to biocompatible products to more demanding requirements such as the ability to incorporate cells, growth factors etc and provide cell-conductive and inductive environments. Many of the currently available degradable polymers do not meet all of these requirements. Furthermore, the development of in-situ polymerizable compositions that can function as cell delivery systems in the form of an injectable liquid/paste are becoming increasingly attractive in tissue engineering applications.

Scaffolds made from synthetic and natural polymers, and ceramics have been investigated extensively for orthopedic repair[6]. This approach has advantages such as the ability to generate desired pore structures and the ability to match size, shape and mechanical properties to suit a variety of applications. However, shaping these scaffolds to fit cavities or defects with complicated geometries, bonding to the bone tissues, and incorporating cells and growth factors, and the requirements of open surgery are a few major disadvantages of the use of known scaffold materials.

The synthetic polymers used in fabricating scaffolds for growing cells belong to the polyester family). For example, poly(glycolic acid) and poly(lactic acid) have been the most commonly used polymers because of their relative ease of degradation under hydrolytic conditions and the degradation products are resorbed to the body. However, these polymers have a number of disadvantages, including rapid loss of mechanical properties, difficulty in processing, and the acidity of degradation products resulting in tissue necrosis[7].

Development of a degradable polymer composition that is ideally flowable and could be injected to fill a defect or cavity has number of advantages. A major advantage would be the possibility of administering a gel arthroscopically in tissue engineering applications avoiding surgery in many cases. Such a polymer would also have the advantage of filling cavities with complex geometries, and of providing good bonding to bone tissue. Incorporation of cells, growth factors and other components to support cell growth could also be incorporated with a gel. Such polymer systems also have the potential to be formulated to generate porous structure upon curing to facilitate nutrient flow to cells during growth and proliferation. Further, such systems may be useful in pre-fabricating scaffolds with complex shapes having appropriate pore structures with biological components already incorporated.

Injectable polymer compositions based on ceramic and synthetic polymers have been reported. Ceramic materials such as calcium phosphate cements have the disadvantage of very slow degradation, which in tissue engineering applications leads to decreased tissue regeneration at the site of the implant, and poor mechanical properties[6]. To overcome some of these problems, injectable compositions based on poly (anhydrides) and poly(propylene fumarate) have been developed. The general method employed includes the preparation of polymerisable precursors with hydrolyzable functional groups in the backbone and curing by free-radical means using either chemical or photo initiation. For example, Mikos and coworkers[8] have developed poly(propylene fumarate) based injectable systems by incorporating mineral fillers to improve mechanical strength. Similarly, Photo-cross-linkable poly(anhydrides) has also been developed for use in orthopedic applications, particularly focusing on achieving high mechanical strength. The systems developed are based on dimethacrylated anhydrides[9]. Both systems require high level of initiators as well as promoters to achieve short curing times. These polymer compositions generally have poor compressive strengths and often require the incorporation of fillers to improve mechanical strength. Photo-curable systems also have the limitation of incomplete curing, particularly in thick samples due to poor light penetration. Further, the above polymer systems have limitations in terms of the options available for tailoring properties for different applications.

Over the last three decades the use of polyurethanes has been explored in biomedical applications due to their excellent mechanical properties and great chemical versatility. Many years of research have resulted in the development of biostable polyurethanes useful for a range of long-term medical implants[10].

Several research groups have reported on preparation and properties of biodegradable polyurethanes based on a range of polyester polyols. Bruin et al[11] reported on the synthesis of biodegradable poly(ester-urethae) elastomer networks by cross-linking star branched L-lactide and glycolide-ε-caprolactone copolymers with ethyl 2,6-diisocyanato hexane (LDI). Saad and coworkers[12-13] reported biodegradable, elastic and highly porous scaffolds based on poly (3-hydroxybutric acid) and poly(caprolactone-co-diethylene glycol) polyols with aliphatic diisocyanates. Bennett et al[14] disclosed polymers useful for surgical devices, based on star polymers of soft segment forming monomers, which can be cross-linked with isocyanates.

Zang et al[15] have described lysine diisocyanate, glycerol and water based biodegradable spongy polyurethanes that may be useful for biomedical applications as suggested based on in-vitro test results. Story et al[16-19] report on the preparation of hydrolysable polyester networks) from L-lysine diisocyanate and D,L-lactide/ε-caprolactone home—and copolyester triols and trimethylene carbonate homoployester and copolyester triols. In these studies hydroxy functional polyester triols were reacted with diisocyanates such as lysine diisocyanate and toluene diisocyanate to form network polyurethanes. Likewise, Bruin et al[20] have reported on biodegradable polyurethanes networks based on LDI and poly (glycolide-co-ε-caprolactone) for fabrication of 2-layer artificial skin.

Spaans et al[21-23] discloses biomedical polyurethane-amides from isocyanate-terminated polyester networks by reacting with dicarboxylic acid or hydroxycarboxylic acid in the presence of sodium chloride crystals to produce macroporous structures suitable for repairing meniscal lesion. Similarly, van Tienen et al[24] reported on the caprolactone/L-lactide based polyurethane networks, fabricated to from porous scaffolds useful for repair of knee meniscus defects.

Woodhouse et al[25] have disclosed a biodegradable polyurethane material having a backbone containing at least one amino acid group suitable for wound dressings.

Notwithstanding the wide reporting of degradable polyurethanes in the literature, there has been relatively little research directed to the development of degradable polyurethanes structurally tailored to be biodegradable for tissue engineering. As a class of synthetic polymers, polyurethanes offer numerous opportunities to tailor materials with properties and chemical composition to suit applications in soft tissue as well as hard tissue engineering applications. Several research papers describe polyurethanes with degradable polyester soft segments and methods to fabricate porous scaffolds that support cell-growth. However, there are no reports on degradable polyurethane-based and desirably injectable polymer systems that can incorporate cells, growth factors and other components to support cell growth as well or on curing such polymer compositions with low heat generation to minimize cell necrosis.

Accordingly, it is an object of the present invention to provide biodegradable, biocompatible polymers that are capable of supporting living and non living biological additives during preparation and use and which are flowable, and preferably injectable. It is a further object to provide prepolymer compositions that may be cured with degradable oligomers ex vivo or in vivo to form the biocompatible, biodegradable polymers useful as scaffolds for tissue engineering.

These polymer prepared will desirably be capable of incorporating biological components such as cells, growth factors, and other components such as nano-particle hydroxyapatite, calcium phosphate and other particles and can be cured in vivo or ex vivo to form solid, porous scaffolds for biomedical applications.

SUMMARY OF THE INVENTION

To this end there is provided star, dendrimer or hyperbranched flowable prepolymer composition comprising the reaction product of isocyanates and low molecular weight multifunctional core molecules having at least two and preferably three or more functional groups that react with said isocyanates to form urethane or urea groups.

Throughout this specification, the term "core molecule" should be taken to mean a molecule which has at least two, and preferably three or more functional groups that can react with isocyanate groups to form urethane or urea groups.

Examples of core molecules include but are not limited to diols, triols, and polyols such as sugar molecules.

Preferably the core molecule has a molecular weight of 400 or less.

Isocyanates suitable for preparation of the flowable prepolymers of the invention are those which are selected from the group consisting of optionally substituted aliphatic, aromatic and hindered isocyanates. Preferably the aliphatic isocyanates are asymmetric in molecular shape since by being so, the rate of curing, and hence hardening of the prepolymer composition may be adjusted.

These prepolymer compositions, when introduced to functional oligomers with degradable arms, may react in-vivo or ex-vivo to form porous or non-porous cross-linked polymers which can be used as tissue engineering scaffolds.

A "functional oligomer" according to the invention is a linear, star, dendrimer or hyperbranched oligomer.

Throughout this specification the term "comprises/comprising" when used is taken to specify the presence of stated features, integers, steps or components but does not preclude the presence or addition of one or more other features, integers, steps, components or groups thereof.

It is surprisingly found that the prepolymer compositions according to the invention have a viscosity which enables them to be utilised in a flowable form, and combined with a cross linker for delayed or slow curing thus making them especially suited to biological applications including tissue engineering and repair. The prepolymer compositions can be sterilized without risk to their physical and chemical characteristics, preferably using gamma radiation to ensure sterility Preferably the viscosity of the prepolymer composition on preparation is about 15,000-200,000 cSt at room temperature.

Preferably the prepolymer composition may incorporate biological and inorganic components selected for their ability to aid tissue repair in vivo, or to create certain physical characteristics in the biocompatible, biodegradable polymer composition prepared from the prepolymer composition. These biological and inorganica components are preferably selected from the group consisting of cells, progenitor cells, growth factors, other components for supporting cell growth, calcium phosphate, hydroxyapatite, nanoparticulate tricalcium phosphate and hydroxyapatite type fillers, adhesives including fibrin, collagen and transglutaminase systems, surfactants including siloxane surfactants, silica particles, powdered silica, hollow fibres which may be used to seed cells in the prepolymer composition, and other porogens including, for example, gelatin beads. The biological and inorganic components may be present in quantities according to need, especially in the case of the living additives such as cells and progenitor cells. Amounts of up to at least 20% w/w may be acceptable.

It is to be noted that a solvent is not essential to maintenance of the prepolymer composition at a viscosity suited to applications wherein flowability and preferably, injectability are desirable. This is especially important in biological applications since many solvents are not biocompatible and may, in fact, be toxic to cell sustainability.

The invention also provides a biodegradable biocompatible polyurethane/urea polymer composition comprising the reaction product of prepolymers prepared according to the invention, and linear star dendrimer or hyperbranched soft segment forming functional oligomers with degradable arms.

"Degradable arms" according to the invention are any molecular moiety which may be part of the functional oligomers with which the prepolymer composition is cross linked, which molecular moiety structure is preferably biocompatible and bioresorbable on in-vivo degradation of the biocompatible, biodegradable polyurethane/urea compositions.

The biocompatible, biodegradable polyurethane/urea compositions are preferably flowable, more preferably injectable and cure with low exotherm so as to make them particularly suited to supporting live biological components. They may be cured ex-vivo and then implanted using invasive medical procedures, or cured in-vivo, after insertion by non-invasive medical methods such as by arthroscope. When cured, the polyurethane/urea compositions according to the invention form a biodegradable biocompatible scaffold which may be porous and contain interpenetrating polymer networks so as to enable the inclusion of biological components such as cells, progenitor cells, growth factors and other components for supporting cell growth. By selecting the components of the prepolymer and the functional oligomers appropriately, the curing time of the biocompatible, biodegradable polyurethane/urea compositions can be varied according to their application. The polymer compositions according to this aspect of the invention are referred to hereinafter as "biocompatible, biodegradable polyurethane/urea compositions".

The invention also provides a biodegradable, biocompatible polymeric scaffold comprising a cured biocompatible, biodegradable polyurethane/urea composition according to the invention.

Preferably the cured scaffolds according to this aspect of the invention have a compressive strength in the range of 0.05-80 MPa. The compressive strength of the scaffold will vary according to its porosity and according to the biological components added.

Preferably the scaffolds have pores in the size range of 150-300 micron. More preferably these pores are formed from hollow fibres incorporated in the prepolymer compositions employed in their production.

More preferably the porous scaffolds are seeded with living biological components selected so as to aid the tissue repair process in the patient being treated. The biological components so selected may be cells, progenitor cells, growth factors and other components for supporting cell growth.

Suitable cells may include osteoblasts, chondrocytes, fibroblasts or other precursor cells.

In another aspect of the invention, there is provided a process for the preparation of a biocompatible, biodegradable polyurethane/urea composition comprising reacting an isocyanate with a core molecule having at least two and preferably three or more functional groups that react with said isocyanate to form urethane or urea groups under suitable conditions to form a prepolymer with a flowable viscosity; and reacting said prepolymer with a star soft segment forming functional oligomer with degradable arms and optionally, appropriate amounts of water and catalyst under conditions such that the reaction temperature does not exceed 90° C., preferably 60° C. and more preferably 40° C.

Preferably the viscosity of the prepolymer formed is about 15,000-200,000 cSt at room temperature.

Preferably, the process further comprises the step of adding biological and inorganic additives selected from the group consisting of cells, progenitor cells, growth factors, other components for supporting cell growth, calcium phosphate, hydroxyapatite, nanoparticulate tricalcium phosphate and hydroxyl apatite, adhesives including fibrin, collagen and transglutaminase systems, surfactants including siloxane surfactants, silica particles, powdered silica, sugars, sodium chloride type salts, hollow fibres which may be used to seed cells in the prepolymer composition, and other porogens including, for example, gelatin beads. More preferably this step is carried out in the formation of the prepolymer composition.

Preferably the process further comprises the step of reacting said prepolymer with high molecular weight degradable polymer. The high molecular weight degradable polymer may be selected from the group consisting of PLGA, PLLA and poly(anhydrides) and serves so as to assist in the establishment of interpenetrating networks of pores.

In another embodiment of the invention there is provided a biodegradable, biocompatible polyurethane/urea composition prepared by reacting an isocyanate with a core molecule having at least two and preferably three or more functional groups that react with said isocyanate to form urethane or urea groups under suitable conditions to form a flowable prepolymer; and reacting said prepolymer with a star soft segment forming functional oligomers with degradable arms and optionally, appropriate amounts of water and catalyst under conditions such that the reaction temperature does not exceed 90° C., preferably 60° C., more preferably 40° C.

Preferably the biocompatible, biodegradable polyurethane/urea compositions so formed are utilizable as tissue engineering scaffolds.

Preferably the viscosity of the prepolymer formed is about 15,000-200,000 cSt at room temperature.

The biocompatible, biodegradable polyurethane/urea compositions so formed are preferably porous.

Preferably the biocompatible, biodegradable polyurethane/urea composition further comprises biological additives selected from the group consisting of cells, progenitor cells, growth factors, other components for supporting cell growth, calcium phosphate, hydroxyapatite, nanoparticulate tricalcium phosphate and hydroxyapatite, adhesives including fibrin, collagen and transglutaminase systems, surfactants including siloxane surfactants, silica particles, powdered silica, sugars, sodium chloride type salts, hollow fibres which may be used to seed cells in the prepolymer composition, and other porogens including, for example, gelatin.

In these embodiments of the invention, it is surprisingly found that whereas in the prior art methods wherein a hard segment polymer is introduced in a second polymerisation step, in the methods according to the invention, the use of soft-segment polymers in the second polymerisation or cross linking step leads to low shrinkage in the second step due to the fact that fewer chemical bonds are needed to produce a cross-linked polymer network. This is especially useful in biological applications wherein a close fit between, for example, a bone cavity, and a temporary polymeric prosthesis is important.

A "hard segment" polymer according to the invention is one which imbues the copolymer with its physical strength which often arises from the alignment or formation of ordered domains of monomers of a common type.

A "soft segment" polymer according to the invention is typically formed from amorphous polyols with higher molecular weight than that of hard segment forming compounds, and does not easily form ordered domains.

In another embodiment of the invention there is provided a method of treatment of damaged bone or cartilage in a patient requiring such treatment, the method comprising administering to said patient a biocompatible, biodegradable polyurethane/urea composition according to the invention, said administration occurring by the implant of a scaffold formed ex-vivo from a cured form of said polyurethane/urea composition, or by the injection of said polymer in an uncured form for in-vivo curing and scaffold formation. The composition may preferably include biological additives to assist in the repair of the damaged bone or cartilage such as cells, progenitor cells, growth factors, or other suitable materials. Biological additives used may preferably include osteoblasts, chondrocytes, fibroblasts, fibrin, collagen, transglutaminase systems and the like.

The invention also provides for the use of biocompatible, biodegradable polyurethane/urea compositions according to the invention as a tissue engineering scaffold for assistance in tissue engineering applications such as bone and cartilage repair.

The biocompatible, biodegradable polyurethane/urea compositions may also be used in methods such as those described in WO 02/062357 (CSIRO and Industrial Technology Research Institute) the contents of which are incorporated herein by cross reference.

Other embodiments of the invention will be evident from the following detailed description of various aspects of the invention.

BRIEF DESCRIPTION OF THE FIGURES

FIG. 12 shows the change in polymer viscosity with curing time at 23° C. according to example 15.

FIG. 13 shows the temperature rise during polymer curing/gelling according to example 16.

FIG. 14 shows Haematoxylin and Eosin staining of a 6 week culture showing cluster of viable stem cells (purple) and new matrix (pink) within hollow fibres (transparent) within the polymer scaffold, according to example 31.

FIG. 15 shows a 6 week culture of human mesenchymal stem cells grown in hollow fibres within the polymer scaffold supplemented with differentiation medium to promote osteoblast differentiation according to example 31. Sample is stained with von Kossa to show bone mineralization (brown/black staining).

FIG. 16 shows Haemotoxylin and Eosin staining of a 4 week culture showing cluster of viable chondrocytes within resorbed gelatin beads within the polymer scaffold according to example 32.

FIG. 17 shows Alcian blue staining of a 9 week culture showing cluster of viable chondrocytes around gelatin beads within the polymer scaffold according to example 32. Pink staining indicates cells and blue around cells indicates new glycosaminoglycan synthesis.

FIG. 18 shows micrographs showing cellular integration into the polymer structure after 2 month implantation in rats (a) Polymer implant sample #1 (b) Polymer implant sample #2 according to example 34.

DETAILED DESCRIPTION OF THE INVENTION

Figure 1:
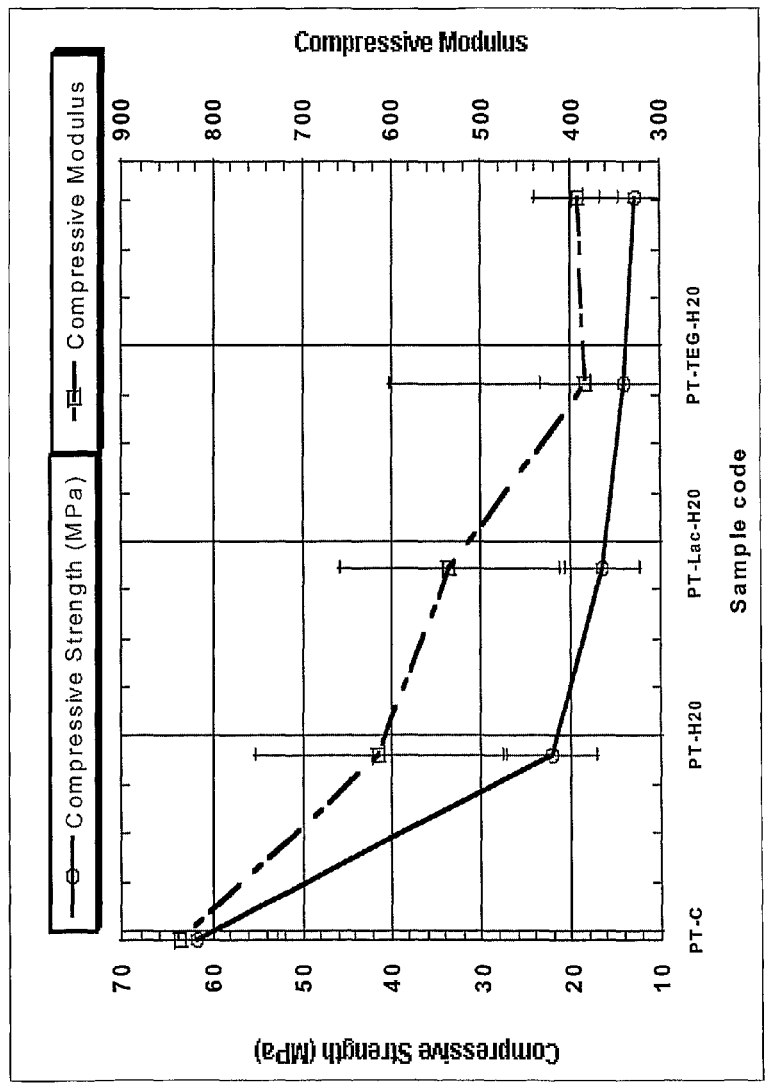
FIG. 1 shows the effect of water, lactose and triethylene glycol on compressive strength on cured polymer scaffolds of the invention.

The present invention relates to star, dendrimer, and hyperbranched prepolymers (referred to hereinafter as Prepolymer A) prepared from a preferably low molecular weight, multifunctional core-molecules and isocyanates. These prepolymers when reacted with functional oligomers, particularly star-shaped molecules with degradable arms (referred to hereinafter as Components B), may cross link in vivo or ex vivo to form porous or non-porous cross-linked polymers suitable for a variety of tissue engineering applications.

According to the present invention, a low molecular weight core molecule is defined as one that has two, and preferably three or more functional groups that can react with isocyanate groups to from urethane or urea groups. For example, pentaerythritol with four hydroxyl groups is a suitable core molecule. A range of other core molecules can be used and some examples are 1. Glycerol
2. Pentaerythritol
3. Dipentaerythritol
4. Tripentaerythritol
5. 1,2,4-Butanetriol
6. Trimethylolpropane
7. 1,2,3-Trihydroxyhexane
8. Myo-inositol
9. Ascorbic acid 10. Glucose and isomers (D-galactose, D-mannose, D-fructose)
11. Maltose
12. Sucrose
13. Mannitol
14. N-Acetyl-D-glucosamine Preferably the core molecule is a star, dendrimer or hyperbranched molecule having molecular weight of 400 or less. The higher the molecular weight of the core molecule selected the less likelihood there is of the formation of a flowable, and preferably injectable prepolymer composition.

Isocyanates suitable for preparing prepolymers according to the present invention are selected from the group consisting of optionally substituted aliphatic, aromatic and hindered isocyanates and are preferably those with isocyanate groups having different reactivities, that is, those that are asymmetric. The optional substitution may occur in the alkyl of the ester group. Examples of such isocyanates include:

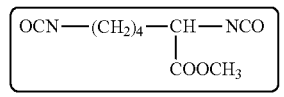

MLDI
methyl 2,6-diisocyanato hexanoate

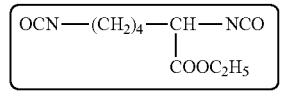

ELDI
ethyl 2,6-diisocyanato hexanoate

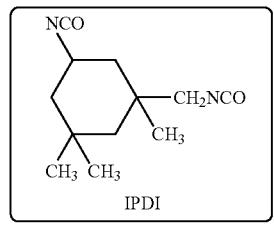

IPDI
isophorone diisocyanate

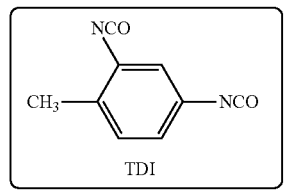

TDI
toluene diisocyanate

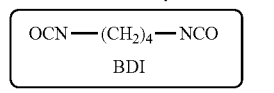

BDI
1,4-butane diisocyanate

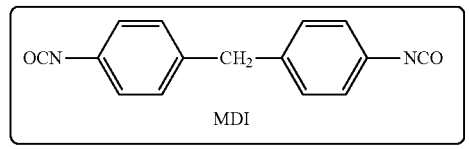

MDI
4,4′methylene diphenyl diisocyanate

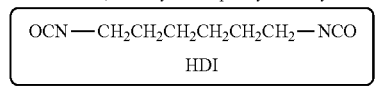

HDI
Hexamethylene Diisocyanate

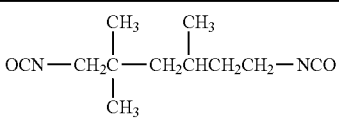

TMHDI
2,2,4-Trimethyl hexamethylene diisocyanate

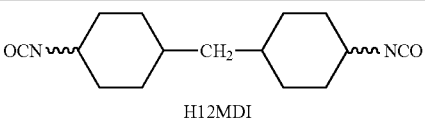

H12MDI
Cyclohexyl Methylene Diisocyanate

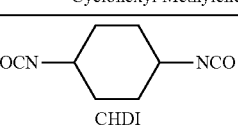

CHDI
1,4-Cyclohexane diisocyanate

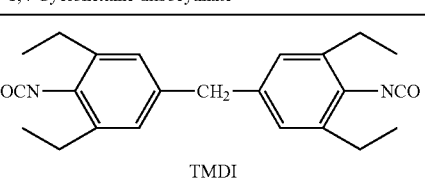

TMDI
Tetraethyl methylene diphenyl diisocyanate

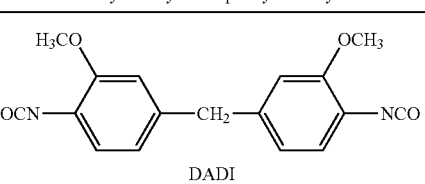

DADI
Dianisidene diisocyanate

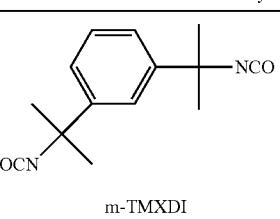

m-TMXDI
m-tetramethyl xylene diisocyanate

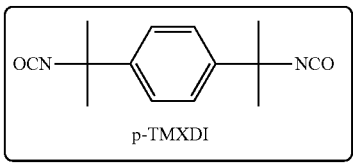

p-TMXDI
p-tetramethyl xylene diisocyanate

According to the present invention, the core molecule and excess isocyanate are preferably reacted without the presence of any solvent to form a star prepolymer. The quantities of the core molecule and isocyanate are stoichiometrically balanced with respect to the NOC and functional groups that can react with it. It is understood that common solvents such as DMF, THF, DMAc commonly used in polyurethane synthesis may be used in making the prepolymer A. However, in general, owing to issues with their biocompatibility, and due to the controlled flowability of the Prepolymer A, solvents will generally not be required. Typical reactions involved are illustrated by example in Scheme-1. Along with star polymers, dendritic and hyper-branched prepolymers are formed during the reaction depending on the reaction conditions and the types of core molecules and isocyanates used.

Scheme 1

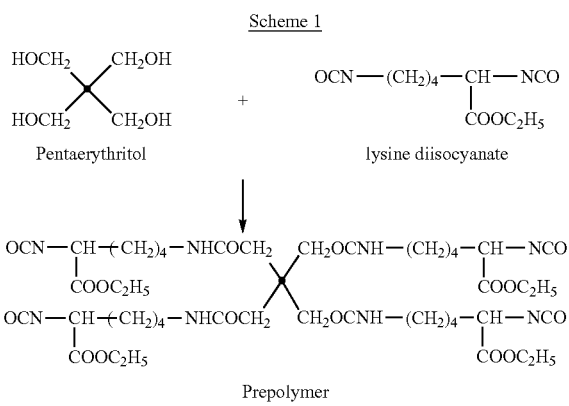

The prepolymer (Prepolymer A) formation reaction may be catalyzed using a range of known catalysts useful in making polyurethanes. Preferred catalysts include stannous octoate, stannous 2-ethyl hexanoate, dibutyltin dilaurate, 1,4-diazabicyclo[2.2.2]octane, triethylamine, and diaminoethanol. Other catalysts that may be useful include tetra n-butyl titanate, titanium acetylacetonate, triethanolamine titanate, titanium ethylaceto-acetate, tetraethyl titanate, tetraisopropyl titanate, titanium lactic acid chelate and other catalysts available under the TYZOR range from DuPont. Catalysis may or may not be utilised depending on the period of time over which it is desired that Prepolymer A remain flowable and injectable. This will depend upon the environment in which the biocompatible, biodegradable polyurethane/urea composition is to be used, ex vivo or in vivo.

The prepolymer A is cured with component B to form biodegradable, biocompatible polyurethane/urea compositions which can be cured to form polymer scaffolds.

Component B functional oligomers having degradable arms which may be used to cross-link the prepolymers of the invention may include lactides, glycolides, lactide/glycolides, caprolactones, propylene fumarates, glycolic acid, dioxanones, anhydrides, polyorthoesters and the like. Functional oligomers which are zwitterionic can be desirable in circumstances where the resultant scaffolds are to be seeded with cells as they support cell growth. Functional oligomers forming component B may be, but are not essentially, soluble in Prepolymer A. In the case that the functional oligomers B are soluble in Prepolymer A, this will aid delivery of the uncured, flowable biodegradable, biocompatible polyurethane/urea compositions of the invention, for example, in some biomedical applications such as in arthroscopic treatments for bone replacement or temporary prosthesis. Particularly suitable functional oligomers and degradable arms may include:

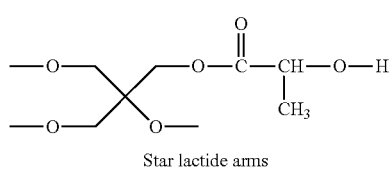

Star lactide arms

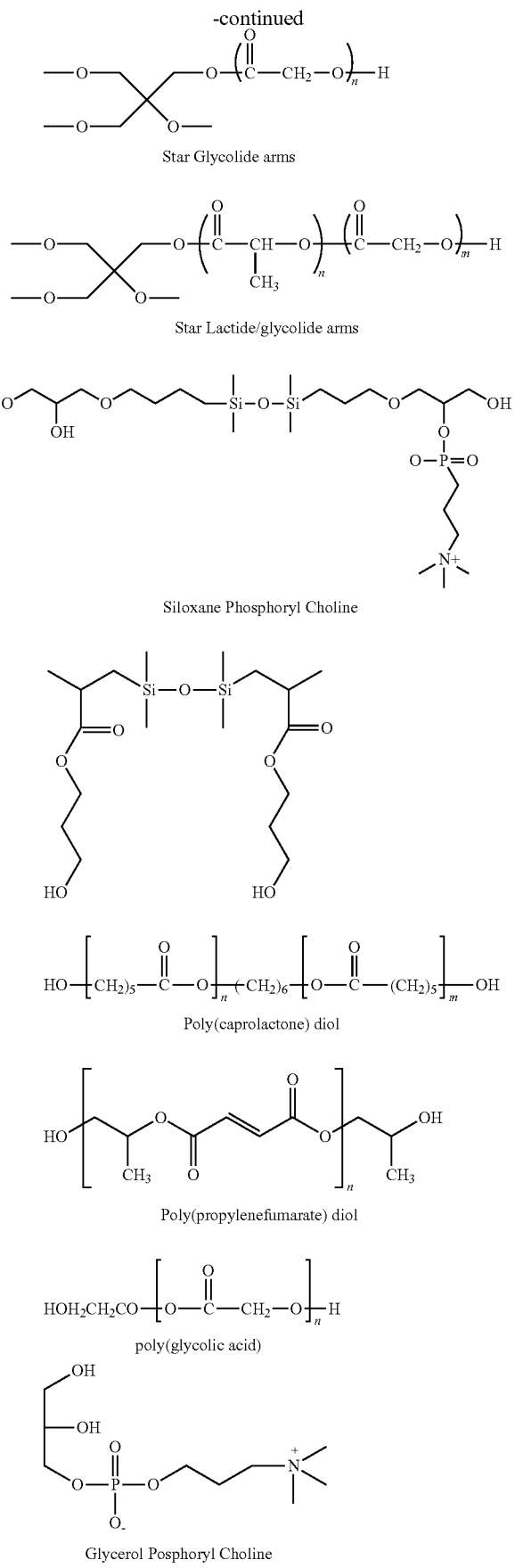

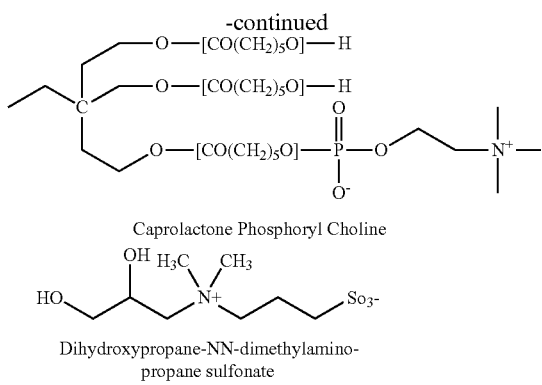

Caprolactone Phosphoryl Choline

Dihydroxypropane-NN-dimethylamino-propane sulfonate

Other suitable functional oligomers and degradable arms include ethyleneglycol/lactides, polycaprolactone triols, dihydroxypolycaprolactones and other phosphoryl cholines.

The functional oligomer having degradable arms, Component B, is particularly selected to import physical properties to cured polymer compositions of the invention.

The curing-cross linking reaction can be carried out under mild temperature conditions. Typically, the reaction is preferably carried out at temperatures ranging from 20° to 30° C. The catalyst concentration can be adjusted such that the temperature of the reaction mixture does not exceed 60° C. more preferably 40° C., and the mixture can change from a viscous liquid to a putty like consistency in about 5 to 45 min.

The mechanical properties of cured scaffolds according to the invention are highly desirable. In particular, the cured scaffolds of the invention have good compressive strength. FIG. 1 shows the effect of water, lactose and triethylene glycol on compressive strength of cured polymer compositions of the invention. They can also be sterilized using, for example, gamma radiation, and will degrade in appropriate time frames by oxidative or hydrolytic degradation.

The biological additives which may be incorporated in either prepolymer A or component B and injected in a tissue or bone repair site, using surgical or arthroscopic techniques may include but are not limited to cells, growth factors, progenitor cells, natural adhesives such as fibrin, collagen or transglutaminase system.

Inorganic fillers such as hydroxyapatite and tricalcium phosphate could be incorporated, preferably as nano-particles to reinforce the cured scaffold, and to support cell growth, particularly osteoblast and chondrocyte type cells, to either prepolymer A or component B. In a preferred embodiment, nano particles are incorporated in component B. The filler particles are dispersed in component B and mixed with prepolymer A to form rigid biodegradable, biocompatible polyurethane/urea compositions. It is speculated that nanoparticles will resorb faster, and accordingly may have an advantage over larger particles.

Water may be added to component B to generate carbon-dioxide to provide porosity in the cured polymer. The amount of water may be controlled depending on the desired pore size and content. Porosity can also be generated by incorporating leachable compounds into either prepolymer A or into the functional oligomer, or into the mixture of the two components. Common porogens include salt and sugar crystals. These leachable compounds could be removed from the cross-linked polymer by soaking in water, or by allowing them to slowly leach out in aqueous environments. It may also be possible to incorporate surfactants including siloxane surfactants so that more water may be incorporated thereby adjusting [pore size and distribution. Other porogens may be used including gelatin beads as described in WO 02/062357.

The biological components will be added in quantities suited to need, particularly in the case of cells, progenitor cells, fibrin, collagen, transglutaminase systems, and other living matter. Indicative amounts of some of the components are as follows. Calcium phosphate may be preferably added in an amount of about 4%. Hydroxyapatite may be added in an amount of about 5%. Collagen may be added in an amount of less than about 0.01%. Siloxane surfactant may be added in an amount of about 5 mol %. Silica particles may be added in an amount of about 5%.

Figure 2:
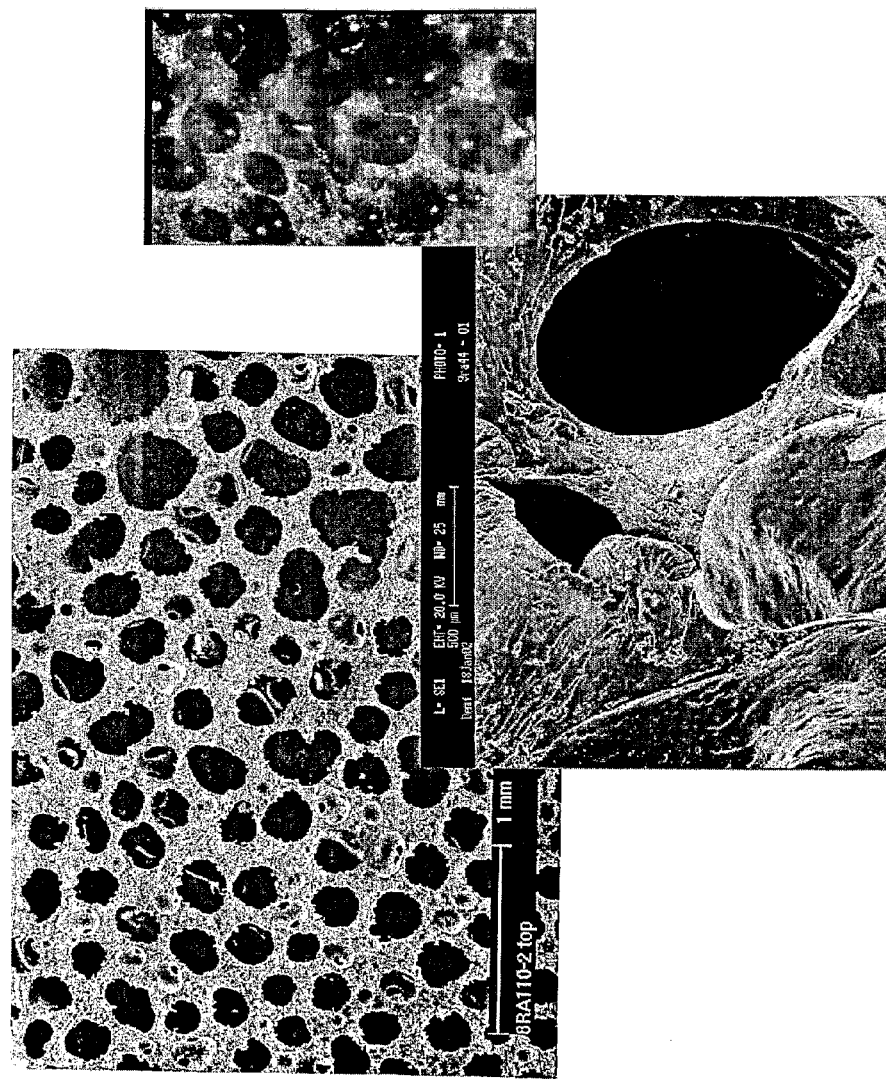
FIG. 2 shows an SEM photograph of a porous polymer scaffold according to the invention.
Figure 3:
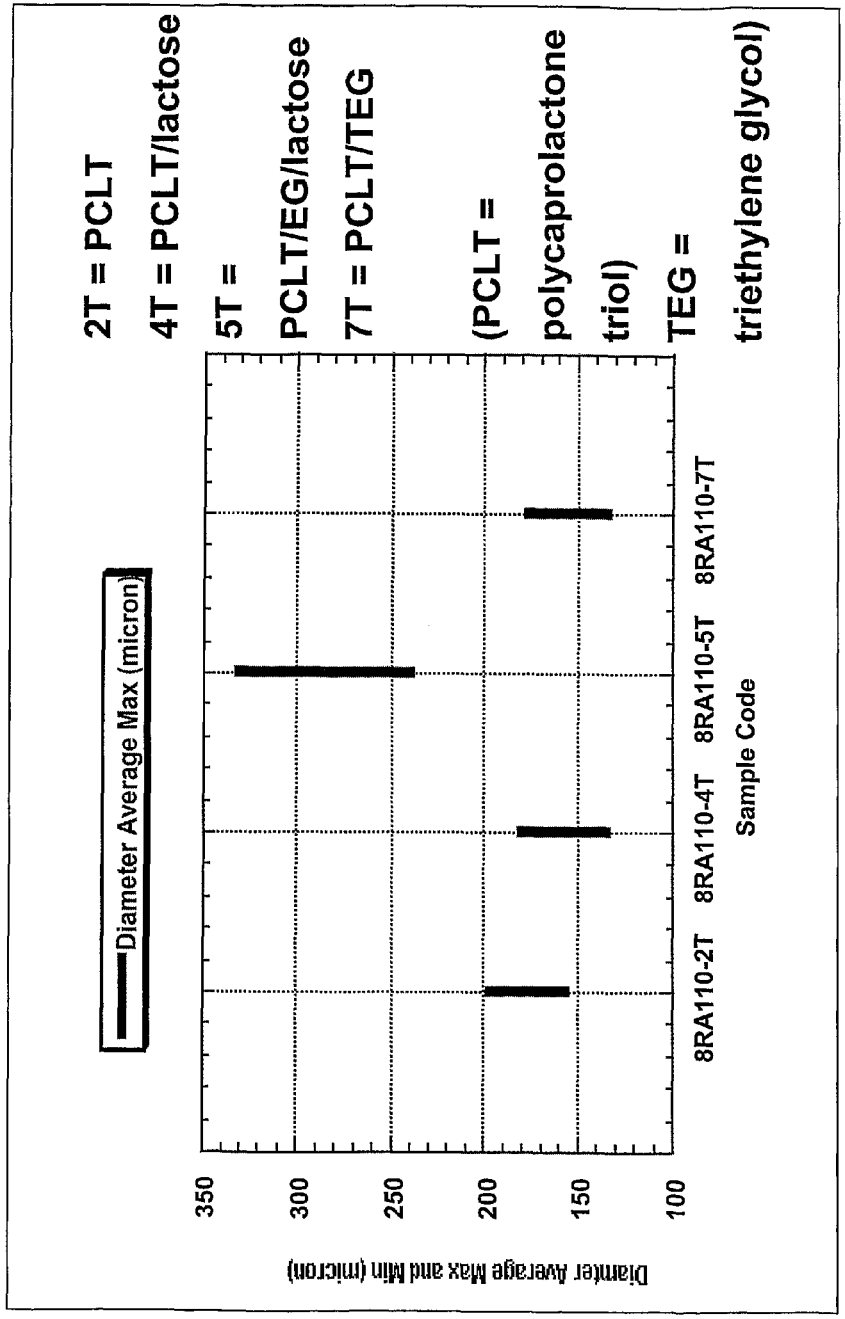
FIG. 3 shows the effect of different degradable functional oligomers on the average porosity of the cured polymer scaffolds of the invention.

In trials conducted to date, porous scaffolds have been constructed and examined under SEM. The results are shown in FIG. 2. The effects of different degradable functional oligomers were determined and the average porosity of the resultant average porosity measured. These results are shown in FIG. 3.

Figure 4:
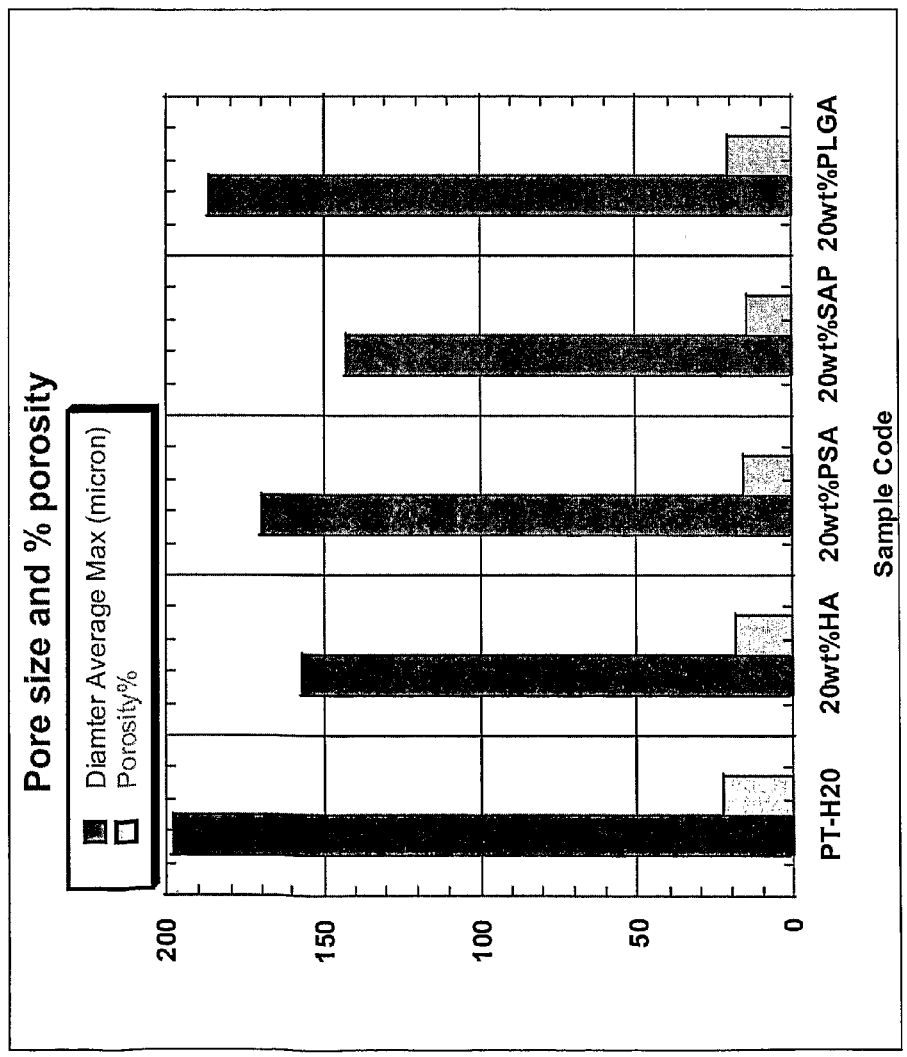
FIG. 4 shows the effect of incorporating high molecular weight degradable polymers and fillers on pore size and distribution in cured scaffolds of the invention.
Figure 5:
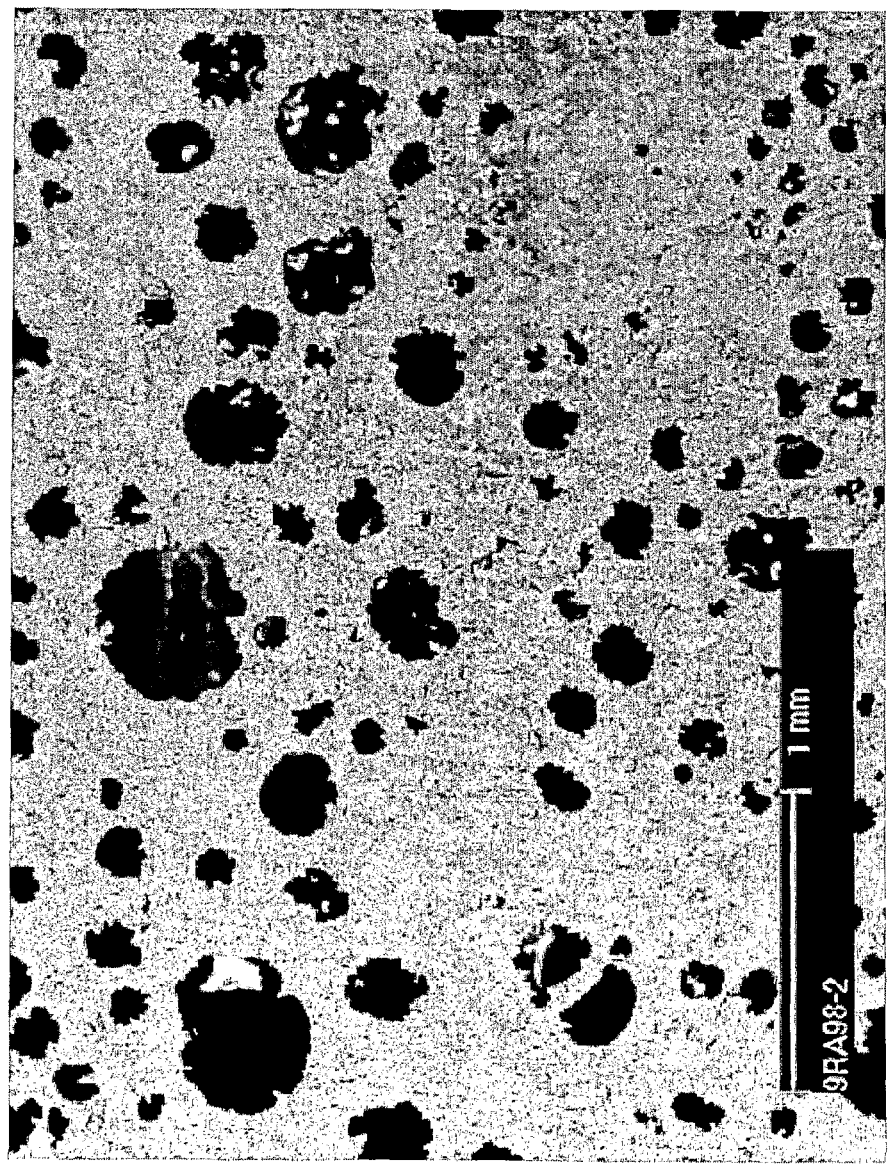
FIG. 5 shows the effect of the incorporation of fillers on pore size and distribution in cured polymer scaffolds of the invention.
Figure 6:
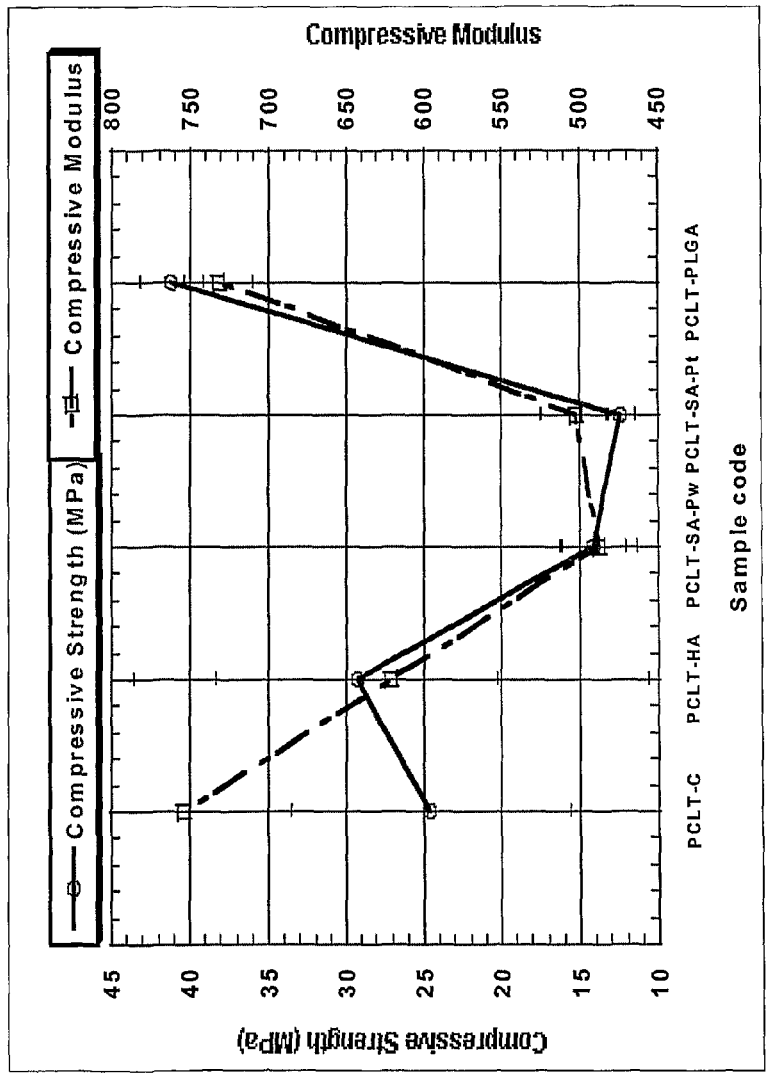
FIG. 6 shows the effect of the incorporation of fillers on the mechanical properties of cured polymer scaffolds of the invention.

The effect of incorporating degradable high molecular weight polymers in component B to form inter-penetrating networks has also been investigated. These insertions enable the varying of degradation rates of the cured polymer composition. PLGA, PLLA and polyanhydrides have been shown to be effective. FIG. 4 shows the effect of incorporating high molecular weight degradable polymers and fillers on pore size and distribution in cured scaffolds of the invention. FIG. 5 also shows the effect of the incorporation of fillers on porosity. FIG. 6 shows the effects of the incorporation of fillers of the mechanical properties of cured scaffolds according to the invention.

Figure 7:
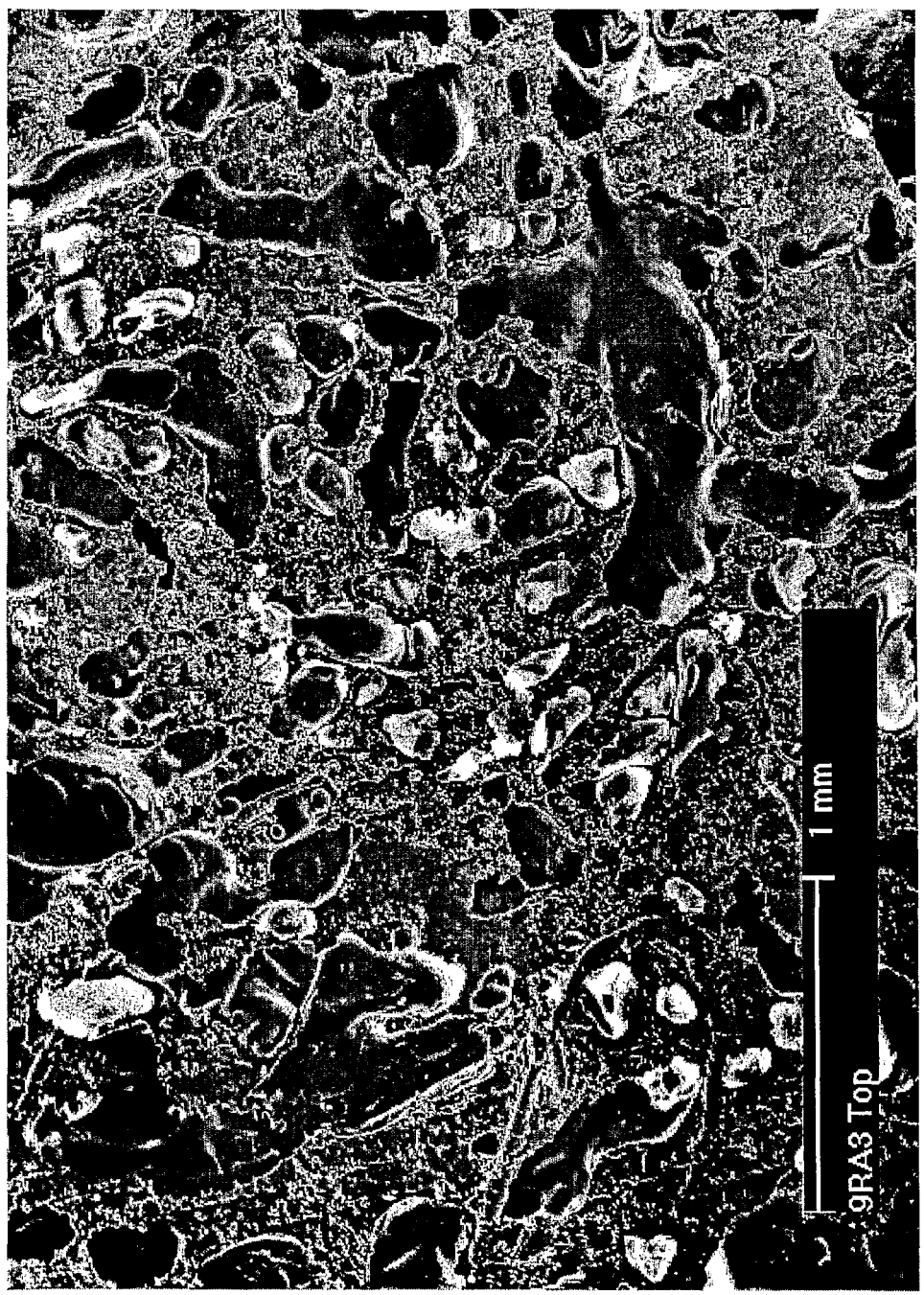
FIG. 7 shows the porosity of cured polymer scaffolds according to the invention incorporation hollow fibres.

Porous hollow fibres made from degradable polymers such as poly(lactide) poly(glycolide) and their copolymers, poly(anhydrides), and other polyesters, may be incorporated with or without cell seeding in the preparation of prepolymer A or in component B. These hollow fibres form channels to provide nutrients for cell growth and also can be used to seed cells and therefore prevent damage to them during the initial mixing process. FIG. 7 shows the porosity of cured polymers according to the invention incorporating hollow fibres.

Figure 8:
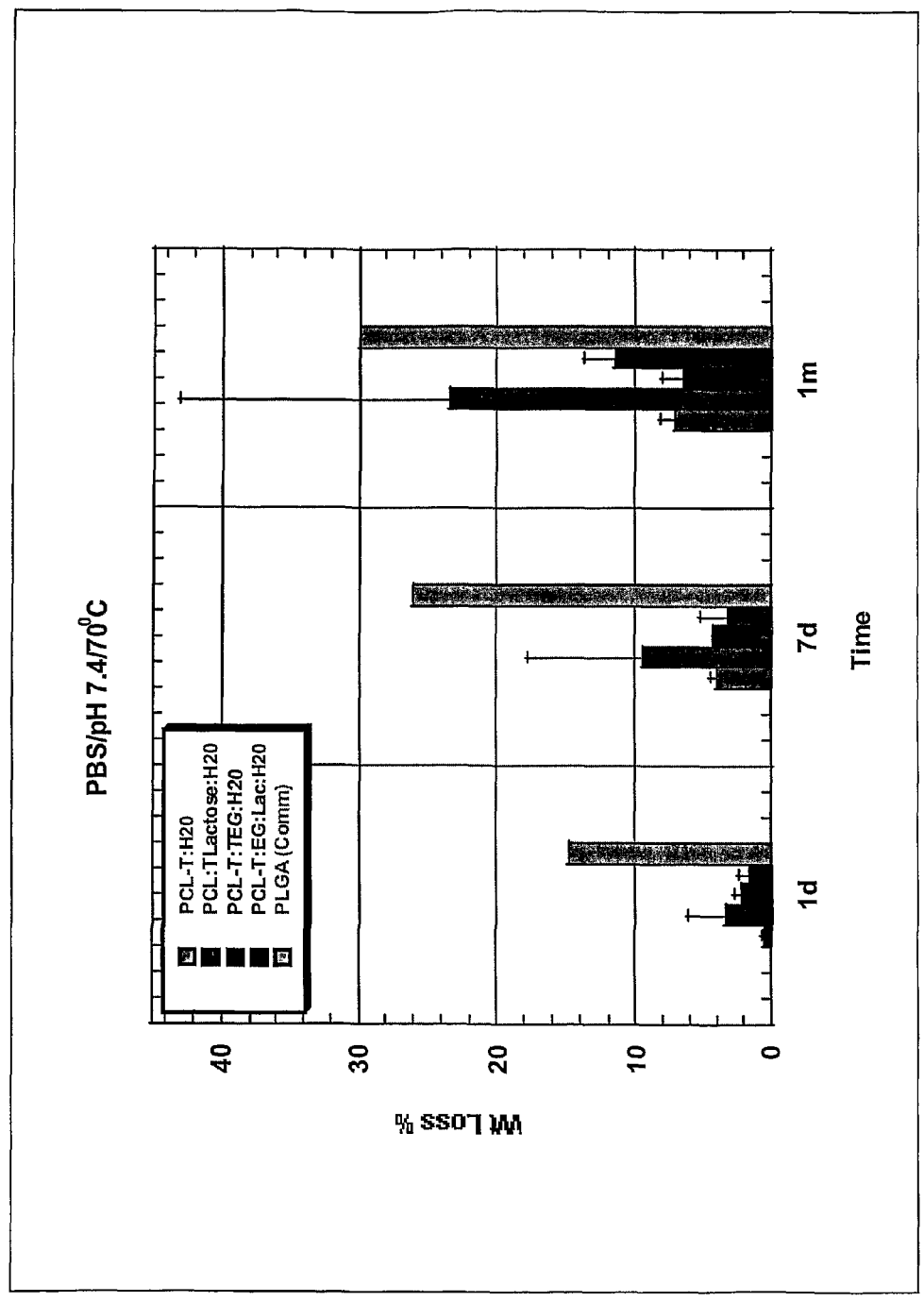
FIG. 8 shows the effect of hydrolytic degradation on various polymer scaffolds according to the invention.

Preliminary degradation studies on cured scaffolds according to the invention have been completed by in-vitro methods. Accelerated hydrolysis (70° C. in PBS, pH 7.4) studies have been completed. FIG. 8 shows the results of hydrolytic degradation on various polymers according to the invention.

Figure 9:
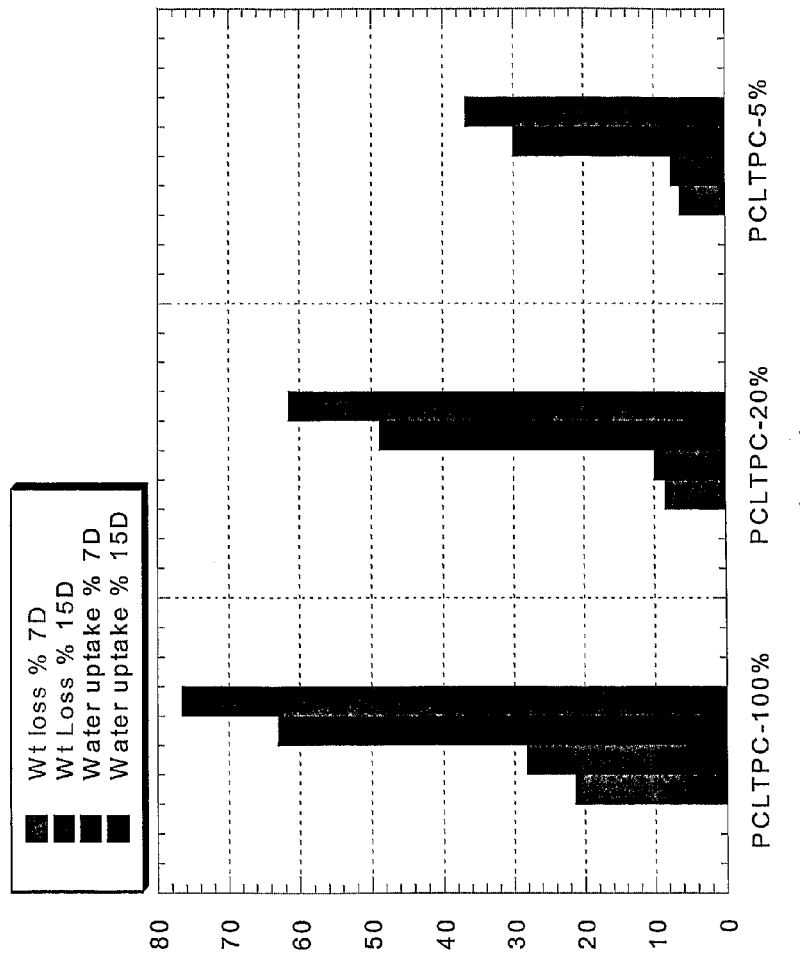
FIG. 9 shows the effect of hydrolytic degradation on polymer scaffolds based on phosphocholine modified polycaprolactone triol.

One preferred cured biodegradable, biocompatible polyurethane/urea composition according to the invention uses as the functional oligomer (component B) phosphocholine modified polycaprolachone triol. Hydrolytic degradation studies on these cured biodegradable, biocompatible polyurethane/urea compositions have been conducted and the results are shown in FIG. 9.

Figure 10:
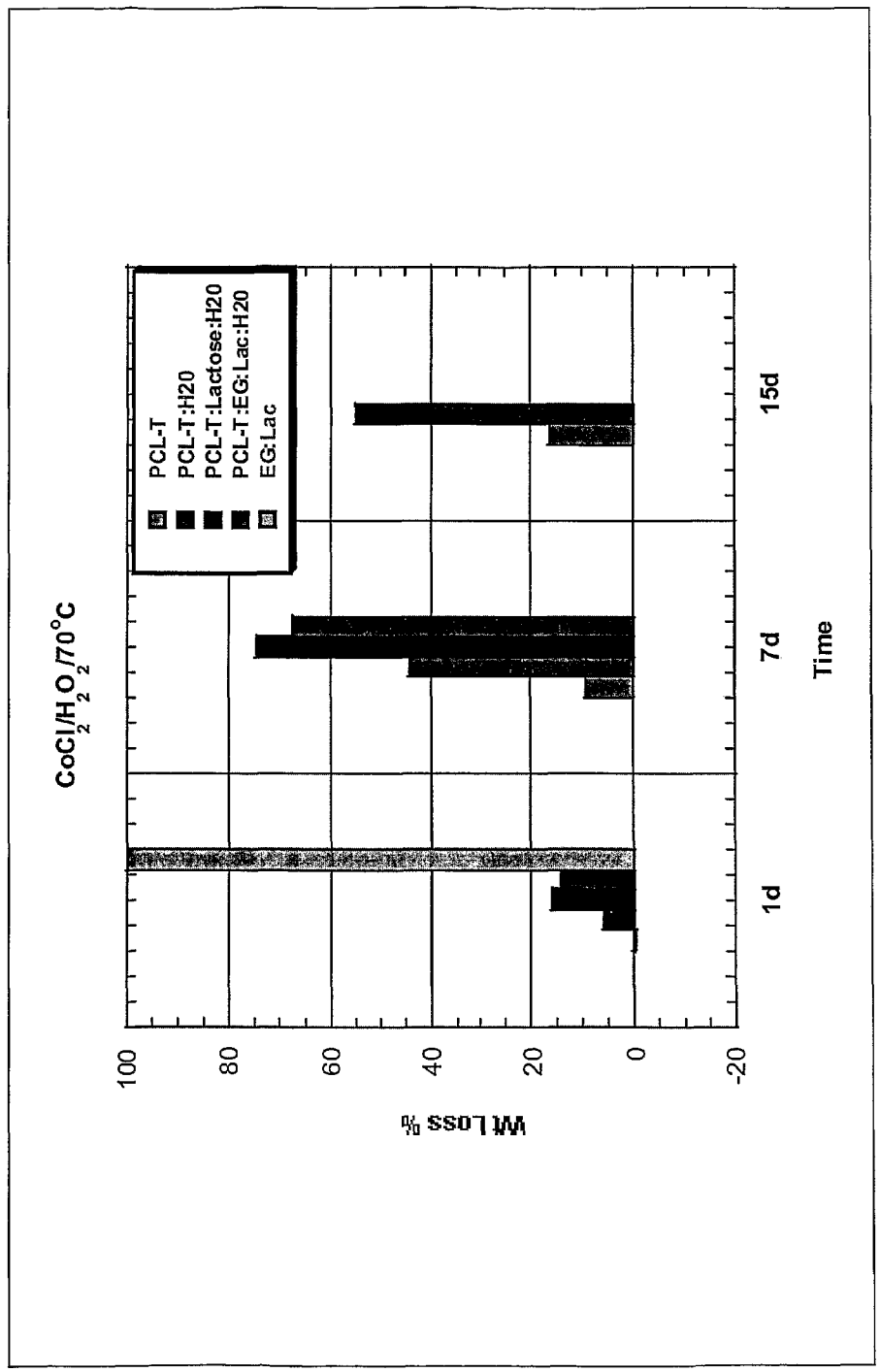
FIG. 10 shows the effect of oxidative degradation on a range of cured polymer scaffolds according to the invention.

Oxidative degradation studies (70° C. in $CoCl_2/H_2O_2$) a range of cured biodegradable, biocompatible polyurethane/urea compositions according to the invention are shown in FIG. 10.

Examples 1 to 5 illustrate the preparation of prepolymer A according to the present invention using a number of different core molecules.

Example 1

Materials:
Pentaerythritol (Aldrich) was dried under vacuum (0.1 torr) at 80° C. over night. Methyl 2,6-diisocyanato hexanoate (MLDI, Kyowa Yuka Co., Ltd, Japan) and stannous 2-ethyl hexanoate (SEH, Sigma Aldrich) were used as received. All the glassware used was thoroughly cleaned and dried at 105° C. overnight in an oven before use.

Predried pentaerythritol (4.818 g) was weighed in a dry three-neck flask equipped with a magnetic stirrer, nitrogen inlet and drying tube. Methyl 2,6-diisocyanato hexanoate (MLDI) (30.04 g) was then added to the flask followed by catalyst stannous 2-ethyl hexanoate (0.1 wt %, 0.0348 g) under nitrogen. The reaction mixture was stirred and heated to 50° C. for 72 h under nitrogen atmosphere. The homogenous polymer mixture was degassed under vacuum (0.1 torr) at 50° C. before it was transferred to a vial under nitrogen atmosphere and stored in the refrigerator. The molecular weight and viscosity of the prepolymer were determined by gel permeation chromatography (GPC) and Bolin Rheometer, respectively.

GPC was performed on Water Associates Liquid Chromatograph system (Waters 717) equipped with a differential refractometer and four μ-Styragel columns ($10^5$, $10^4$, $10^3$ and 100 Å). The mobile phase was tetrahydrofuran (THF) at a flow rate of 1 mL/min. Prepolymer was dissolved in THF by warming the solution at 50° C. for 1 h and filtered through 0.45 micron filter before analysis. The system was calibrated with narrow disperse polystyrene standards and molecular weights are reported as polystyrene equivalents.

The viscosity was measured using Bohlin Rheometer (CSR10) at 23° C.

The number average molecular weight and polydispersity of the prepolymer were 1348 and 1.73, respectively based on GPC analysis. The prepolymer instantaneous viscosity was $8.7 \times 10^4$ cSt.

Example 2

Materials:

Tripentaerythritol (Aldrich) was dried overnight under vacuum (0.1 torr) at 80° C. MLDI and SEH were used as received.

Tripentaerythritol (6.98 g) was weighed in to a dry three-neck round bottom flask equipped with a magnetic stirrer, nitrogen inlet and drying tube. Methyl 2,6-diisocyanato hexanoate (31.81 g) was weighed separately and added to the flask followed by catalyst stannous 2-ethyl hexanoate (0.1 wt %, 0.038 g) under nitrogen. The reaction mixture was stirred and heated at 50° C. for 7 days under nitrogen atmosphere. The homogenous polymer mixture was degassed under vacuum (0.1 torr) at the above temperature for about an hour before it was transferred to a vial under nitrogen atmosphere and stored in the refrigerator. Prepolymer was analysed for molecular weight and viscosity using the methods described in Example 1.

The number average molecular weight and polydispersity of the prepolymer were 827 and 1.36, respectively. The instantaneous viscosity was $3.2 \times 10^4$ cSt Example 3

Materials:

D-Glucose (Aldrich) was dried overnight in a vacuum oven (0.1 torr) at 80° C. MLDI and stannous 2-ethyl hexanoate were used as received.

Predried D-Glucose (5.0 g) was weighed in to a dry three-neck round bottom flask equipped with a magnetic stirrer, nitrogen inlet and drying tube. Methyl 2,6-diisocyanato hexanoate (MLDI) (29.44 g) was then weighed separately and added to the flask followed by catalyst stannous 2-ethyl hexanoate (0.1 wt %, 0.0348 g) under nitrogen. The reaction mixture was stirred and heated at 50° C. for 72 h under nitrogen atmosphere. The homogenous polymer mixture with then degassed under vacuum (0.1 torr) at 50° C. before it was transferred to a vial under nitrogen atmosphere and stored in the refrigerator. The prepolymer was analysed by GPC and Rheometer (CLR-10) using methods described in Example 1.

The prepolymer number average molecular weight was 1430 and the polydispersity was 1.75. Instantaneous viscosity was $1.5 \times 10^5$ cSt at 23° C.

Example 4

Materials:

Ascorbic acid (Aldrich) was dried overnight in a vacuum oven (0.1 torr) at 80° C. MLDI and stannous 2-ethyl hexanoate were used as received.

Predried ascorbic acid (5.15 g) was weighed in to a dry three-neck round bottom flask equipped with a magnetic stirrer, nitrogen inlet and drying tube. Methyl 2,6-diisocyanato hexanoate (24.57 g) was added to the flask followed by catalyst stannous 2-ethyl hexanoate (0.1 wt %, 0.029 g) under nitrogen. The reaction mixture was stirred and heated to 50° C. for 9 d under nitrogen atmosphere. The homogenous polymer mixture was degassed under vacuum (0.1 torr) at 50° C., transferred to a vial under nitrogen atmosphere and stored in the refrigerator. The prepolymer was analysed by GPC and Rheometer using methods described in Example 1.

The prepolymer number average molecular weight and polydispersity were 672, and 1.12, respectively.

Example 5

Materials:

Glycerol (Aldrich) was dried under vacuum (0.1 torr) for three hours at 80° C. MLDI was used as received.

Predried Methyl 2,6-diisocynato hexanoate (41.47 g) was weighed in to a dry three-neck round bottom flask equipped with a magnetic stirrer, nitrogen inlet and drying tube. Glycerol (6.0 g) was weighed separately and added drop wise to the flask at 70° C. and after the addition is over the reaction mixture was heated for 8 h under nitrogen. The prepolymer was clear and homogeneous. The prepolymer was then degassed under vacuum (0.1 torr), transferred to a vial under nitrogen atmosphere and stored in the refrigerator. The prepolymer was analysed by GPC according to the method described in Example 1.

The number average molecular weight of the prepolymer was 1541, while the polydispersity was 1.81.

Examples 6 to 8 illustrate the preparation of Prepolymer A using different diisocyanates.

Example 6

Materials:

Pentaerythritol was dried as described in Example 1. Isophorone diisocyanate (IPDI, Aldrich) and stannous 2-ethyl hexanoate were used as received.

Predried pentaerythritol (5.00 g) was weighed in to a dry-three neck flask equipped with a magnetic stirrer, nitrogen inlet and drying tube. Isophorone diisocyanate (IPDI) (32.65 g) was weighed separately and added to the flask followed by catalyst stannous 2-ethyl hexanoate (0.1 wt %, 0.037 g) under nitrogen. The reaction mixture was stirred and heated to 50° C. for 55 h under nitrogen atmosphere. The homogenous polymer mixture was degassed under vacuum (0.1 torr) at 50° C., transferred to a vial under nitrogen atmosphere and stored in the refrigerator. The prepolymer was analysed by GPC using the method described in Example 1.

The prepolymer number average molecular weight was 1407 and polydispersity 1.21.

Example 7

Materials:
Pentaerythritol was dried as described in Example 1. Hexamethylene diisocyanate (HDI, Aldrich) and stannous 2-ethyl hexanoate were used as received.

Predried pentaerythritol (5.00 g) was weighed in to a dry three-neck round bottom flask equipped with a magnetic stirrer, nitrogen inlet and drying tube. Hexamethylene diisocyanate (24.71 g) was then weighed separately and added to the flask followed by catalyst stannous 2-ethyl hexanoate (0.029 g, 0.1 wt %) under nitrogen. The reaction mixture was stirred and heated to 50° C. for 72 h under nitrogen atmosphere. The homogenous polymer mixture was then degassed under vacuum (0.1 torr) at 50° C., transferred to a vial under nitrogen atmosphere and stored in the refrigerator. The prepolymer was analysed by GPC using the method described in Example 1.

The number average molecular weight and polydispersity of the prepolymer were 1083 and 1.52, respectively.

Example 8

Materials:
D-Glucose was dried as described in Example 3. Ethyl 2,6-diisocyanato hexanoate (ELDI, Kyowa Yuka Co., Ltd, Japan) and stannous 2-ethyl hexanoate were used as received.

Predried D-Glucose (5.0 g) was weighed in to a dry three-neck round bottom flask equipped with a magnetic stirrer, nitrogen inlet and drying tube. Ethyl 2,6-diisocyanato hexanoate (Ethyl-LDI) (31.38 g) was weighed separately and added to the flask followed by stannous 2-ethyl hexanoate (0.1 wt %, 0.036 g) under nitrogen. The reaction mixture was stirred and heated to 50° C. for 72 h under nitrogen atmosphere. The homogenous polymer mixture was then degassed under vacuum (0.1 torr) at the above temperature and was transferred to a vial under nitrogen atmosphere and stored in the refrigerator. The prepolymer was analysed by GPC using the method described in Example 1.

Prepolymer GPC analysis showed a number average molecular weight of 1510 and polydispersity of 2.5. Instantaneous viscosity was $2.6 \times 10^4$ cSt at 23° C.

Example 9

This example illustrates the preparation of prepolymer without the use of a catalyst.

Materials:
D-Glucose (Aldrich) was dried overnight in a vacuum oven (0.1 torr) at 80° C. Methyl 2,6-diisocyanato hexanoate (MLDI) was used as received.

Predried D-Glucose (5.0 g) was weighed in to a dry three-neck round bottom flask equipped with a magnetic stirrer, nitrogen inlet and drying tube. MLDI (29.44 g) was then weighed and added to the flask. The reaction mixture was stirred and heated at 100° C. for 6 d under nitrogen atmosphere. The homogenous polymer mixture was degassed under vacuum (0.1 torr) at the above temperature, transferred to a vial under nitrogen atmosphere and stored in the refrigerator. The prepolymer was analysed by GPC and Rheometer (CSR-10).

The prepolymer number average molecular weight was 1333 and the polydispersity 1.81. Instantaneous viscosity was $1.2 \times 10^5$ cSt at 23° C.

Example 10

Materials:
Pentaerythritol tetrakis (3-mercaptopropionate) (PETMP, Aldrich) was dried under vacuum (0.1 torr) at 90° C. for three hours. MLDI was used as received.

Predried PETMP (10.0 g) was weighed in to a dry three-neck round bottom flask equipped with a magnetic stirrer, nitrogen inlet and drying tube. Methyl 2,6-diisocynato hexanoate (MLDI) (17.37 g) was then weighed separately and added to the flask. The reaction mixture was stirred and heated at 70° C. for 72 h under nitrogen atmosphere. The homogenous polymer mixture was then degassed under vacuum (0.1 torr) at the above temperature before it was transferred to a vial under nitrogen atmosphere and stored in the refrigerator. The prepolymer was analysed by GPC and Rheometer (CSR-10) using methods described in Example 1.

The prepolymer number average molecular weight was 1564 and the polydispersity was 1.94. Instantaneous viscosity was $7.5 \times 10^4$ cSt at 23° C.

Examples 11-14 illustrate the preparation of porous and non-porous polymers using the prepolymer prepared in Example 1.

Example 11

Materials:
Prepolymer of MLDI and pentaerythritol was prepared according to Example 1. Polycaprolactone triol (MW 300, PCLT-300, Aldrich) was dried by heating under vacuum (0.1 torr) at 90° C. for three hours.

Degassed prepolymer (2.20 g) prepared in Example 1 was weighed into a cavity (20×20×10 mm) made in a Teflon block. Degassed and dried polycaprolactone triol (MW 300, 0.80 g) was added to this prepolymer followed by water (0.008 g). The mixture was stirred for few seconds and then stannous 2-ethyl hexanoate catalyst (0.003 g, 0.1%) was added and stirred further for 5 min. This prepolymer mixture remained a viscous liquid and was taken into a 2.5 ml syringe and dispensed 0.29 g to each of the cylindrical (6 D×12 H mm size) cavities in a Teflon mould, sealed and cured overnight at 38° C. to give porous cylindrical test specimens. The cured polymer samples were tested using Instron (Model 5568) for compressive strength and modulus according to ASTM method F451-95.

The average compressive strength and modulus were 22.2±4.6 MPa and 613±138 MPa, respectively.

Figure 11:
FIG. 11 shows an SEM photograph of a cured polymer scaffold prepared according to example 11.

A sample of the cured polymer was examined by Scanning Electron Microscopy to evaluate the polymer porosity. A representative micrograph is shown in FIG. 11 which illustrates that the cured polymer sample is porous.

Example 12

Materials:
Prepolymer of MLDI and pentaerythritol was prepared according to Example 1. Polycaprolactone triol (MW 300, PCLT-300, Aldrich) was dried by heating under vacuum (0.1 torr) at 90° C. for three hours. Nanoparticles (50-100 nm) of hydroxyapatite (Aldrich) was incorporated into PCL-300 by dispersion method Degassed prepolymer (1.13 g) prepared in Example 1 was weighed in to a cavity (20×20×10 mm) made in a Teflon block. Degassed and dried polycaprolactone triol containing 5 wt % nanoparticles of hydroxyapatite (MW 300, 0.41 g) was added to this prepolymer followed by water (0.004 g). The mixture was stirred using a spatula for few seconds and then stannous 2-ethyl hexanoate catalyst (0.0015 g, 0.1%) was added and stirred further for few min. This prepolymer mixture remained a viscous liquid and was taken into a 2.5 ml syringe and dispensed 0.29 g to each of the cylindrical (6 D×12 H mm size) cavities in a Teflon mould, sealed and cured overnight at 38° C. to give porous cylindrical test specimens. The cured polymer samples were tested using Instron (Model 5568) for compressive strength and modulus according to ASTM method F451-95.

The average compressive strength and modulus were 14.4±3 MPa and 512±115 MPa, respectively.

Example 13

Materials:
Prepolymer of MLDI and pentaerythritol was prepared according to Example 1. Polycaprolactone triol (MW 300, PCLT-300, Aldrich) was dried by heating under vacuum (0.1 torr) at 90° C. for three hours. Lactose was dried overnight under vacuum (0.1 torr) at 80° C.

Degassed prepolymer (1.24 g) prepared in Example 1 was weighed in to a cavity (20×20×10 mm) made in a Teflon block. Degassed and dried polycaprolactone triol (0.32 g) and Lactose (0.056 g) water (0.0045 g). The mixture was manually stirred for a few seconds and then stannous 2-ethyl hexanoate catalyst (0.0016 g, 0.1%) was added and stirred further for few minutes. This prepolymer mixture remained a viscous liquid and was taken into a 2.5 ml syringe and dispensed 0.29 g to each of the cylindrical (6 D×12 H mm size) cavities in a Teflon mould and cured overnight at 38° C. to give porous cylindrical test specimens. The cured polymer samples were tested using Instron (Model 5568) for compressive strength and modulus according to ASTM method F451-95.

The average compressive strength and modulus were 16.6±4 MPa and 536±122 MPa, respectively.

Example 14

Degassed prepolymer (3.61 g) of pentaerythritol and MLDI prepared in Example 1 was weighed in to a cavity (2×2×1 cm) made in a Teflon block. Degassed polycaprolactone triol of molecular weight MW 300 (1.46 g) was added to prepolymer followed by 0.1 wt % of 2-ethyl hexanoate catalyst. The polymer mixture was stirred for few minutes manually using a spatula. The viscous polymer was taken into a 2.5 ml syringe and dispensed 0.45 g into each cylindrical cavity (6 mm D×12 mm L) in a multi-cavity Teflon mould and cured overnight at 38° C. to give non-porous cylindrical polymer test specimens.

The cured polymer samples were tested using Instron (Model 5568) for compressive strength and modulus according to ASTM method F451-95.

The polymer samples exhibited 61.9±5.3 MPa, and 837±216 MPa average compressive strength and modulus, respectively.

Example 15

Materials:
Prepolymer of MLDI and pentaerythritol was prepared according to Example 1. Polycaprolactone triol (MW 300, PCLT-300, Aldrich) was dried by heating under vacuum (0.1 torr) at 90° C. for three hours. Prepolymer was degassed under vacuum (0.1 torr) at 50° C. for 20 min with stirring.

Degassed prepolymer (1.0 g) based on pentaerythritol and MLDI prepared according to Example 1 was weighed separately into two cavities (20×20×10 mm) made in Teflon blocks. Dried polycaprolactone triol (MW 300, 0.406 g) was added to prepolymer in one cavity and the mixture was stirred for a few seconds. Catalyst stannous 2-ethyl hexanoate (0.1% based on total weight of prepolymer A and PCLT) was added and stirred. The viscosity of the reaction mixture was monitored using a Rheometer (CLR-10) at 23° C. FIG. 2 illustrates the change in viscosity over that period. Similarly, the second sample was prepared by adding dried polycaprolactone triol (MW 300, 0.406 g) and stannous 2-ethyl hexanoate (0.8% based on total weight of prepolymer A and PCLT) and the viscosity was monitored using the Rheometer. The reaction gel time in the second sample was significantly shorter as illustrated by the higher viscosity shown in FIG. 2.

Example 13 to 16 illustrate the preparation of polymers based on a range of commercially available as well as laboratory synthesized polyols (prepolymer B) and their mixtures as well as the preparation of polymers with additives such as nanoparticle fillers for improvement of mechanical strength.

Example 16

Materials:
Prepolymer of MLDI and pentaerythritol was prepared according to Example 1. Polycaprolactone triol (MW 300, PCLT-300, Aldrich) was dried by heating under vacuum (0.1 torr) at 90° C. for three hours. Prepolymer was degassed under vacuum (0.1 torr) at 50° C. for 20 min under stirring.

Degassed prepolymer (0.564 g) of pentaerythritol and MLDI prepared in Example 1 was weighed in to a cavity (20×20×10 mm) made in a Teflon block. Polycaprolactone triol (MW 300, 0.206 g) was added to this prepolymer followed by water (0.002 g). The mixture was stirred for few seconds and then stannous 2-ethyl hexanoate catalyst (0.0046 g, 0.6% based on total weight of prepolymer, PCLT and water) was added and stirred with a thermocouple probe dipped into the reaction mixture to monitor the reaction temperature. The catalyst concentration in this experiment was adjusted to achieve fast reaction and short gel time. The maximum temperature reached was 40° C. as shown by the temperature profile in FIG. 13.

Example 17

Materials:
Prepolymer prepared in Example 1 was used in this experiment. Polycaprolactone triol (MW 300, PCLT-300, Aldrich) was dried by heating under vacuum (0.1 torr) at 90° C. for three hours. Prepolymer was degassed under vacuum 0.1 torr at 50° C. for 20 min under stirring.

A polyol based on ethylene glycol and lactide (EG:Lactide) was prepared according to the following procedure.

Recrystallised lactide (5.77 g, MW 144, 0.0401 mol) and ethylene glycol (131.73 g, MW 62.02, 2.12 mol) were placed in a dry 500 mL round bottom flask fitted with a suba seal, condenser and nitrogen inlet. The flask was purged with nitrogen overnight and then heated to 90° C. for 1 h in an oil bath. The reaction temperature was raised to 135° C. and heated for further 3 days. The reaction was cooled down to 55° C. and excess ethylene glycol was completely removed at 55° C. under vacuum (0.02 torr) to yield a colourless liquid. $^1$H and $^{13}$C NMR supported the structure of the product.

(Ref: Makromol. Chem., 193, 1623-1631, 1992 J. of Polym. Science: Part A: Polymer Chemistry, Vol. 39, 973-985, 2001. and Macromol. Chem. Phys. 201, 11, 1067-1076, 2000.)

Degassed prepolymer (2.17 g) of pentaerythritol with MLDI prepared in Example 1 was weighed in to a cavity (20×20×10 mm) made in a Teflon block. Degassed and dried polycaprolactone triol of molecular weight (MW 300, 0.572 g) and EG:lactide polyol (MW 134, 0.147 g) were added to this prepolymer followed by water (0.008 g). The mixture was stirred for a few seconds and then stannous 2-ethyl hexanoate catalyst (0.0028 g, 0.1 wt % of based on total weight of prepolymer, PCLT and water) was added and stirred further for 5 min. The mixture which was a viscous and injectable liquid was then taken into a 2.5 ml syringe and dispensed 0.45 g samples into each cylindrical cavity (6 mm D×12 mm H) in a multi-cavity Teflon mould, sealed and cured overnight at 38° C. to give porous cylindrical polymer test specimens.

The cured polymer samples were tested using Instron (Model 5568) for compressive strength and modulus according to ASTM method F451-95.

The polymer samples exhibited 12.8±4.1 mpa, and 393±47 MPa average compressive strength and modulus, respectively.

Example 18

Materials:

Prepolymer prepared in Example 1 was used in this experiment. Polycaprolactone diol (MW 1000, PCLD-1000, Aldrich) was dried by heating under vacuum (0.1 torr) at 90° C. for three hours. Prepolymer was degassed under a vacuum (0.1 torr) at 50° C. for 20 minutes with stirring.

Degassed prepolymer (1.40 g) of pentaerythritol with MLDI prepared in Example 1 was weighed in to a cavity (20×20×10 mm) made in a Teflon block. Degassed and dried polycaprolactone diol of molecular weight (MW 1000, 2.57 g) and water (0.005 g) was added to the prepolymer. The mixture was stirred for few seconds and then stannous 2-ethyl hexanoate catalyst (0.004 g, 0.1% based on based on total weight of prepolymer, PCLD and water) was added and stirred further for 5 min. The mixture which was a viscous and injectable liquid, was taken into a 2.5 ml syringe and dispensed 0.29 g into each cylindrical cavity (6 mm D×12 mm L) in a multi-cavity Teflon mould, sealed and cured overnight at 38° C. to give porous cylindrical polymer test specimens.

The cured polymer samples were tested using Instron (Model 5568) for compressive strength and modulus according to ASTM method F451-95.

The polymer samples exhibited 1.5±0.8 MPa, and 2.7±1.0 MPa average compressive strength and modulus, respectively.

Example 19

Materials:

Prepolymer prepared in Example 8 was used in this experiment. Polycaprolactone triol (MW 300, Aldrich) was dried by heating under vacuum (0.1 torr) at 90° C. for three hours.

Degassed prepolymer (2.27 g) of D-glucose with ELDI prepared in Example 8 was weighed in to a cavity (2×2×1 cm) made in a Teflon block. Degassed and dried polycaprolactone triol of molecular weight (MW 300, 0.77 g) and water (0.007 g) was added to the prepolymer. The mixture was stirred for few seconds and then 0.1 wt % of stannous 2-ethyl hexanoate catalyst (0.003 g, 0.1% based on based on total weight of prepolymer, PCLT and water) was added and stirred further for 5 min. The mixture which was a viscous and injectable liquid was taken into a 2.5 ml syringe and dispensed 0.29 g into each cylindrical cavity (6 mm D×12 mm H) in a multi-cavity Teflon mould, sealed and cured overnight at 38° C. to give porous cylindrical polymer test specimens.

The cured polymer samples were tested using Instron (Model 5568) for compressive strength and modulus according to ASTM method F451-95.

The polymer samples exhibited 8.6±0.4 MPa, and 109±11 MPa average compressive strength and modulus, respectively.

Example 20 describes the method of preparing prepolymers dihydroxypolycaprolactone phosphoryl choline (DP-CLPC) and synthesis of dihydroxyglycerol phosphoryl choline (DGPC).

Example 20

Dihydroxypolycaprolactone phosphoryl choline (DP-CLPC) was prepared using a modified literature reported procedure (Ref; Polymer J, 22, p 355-360, (1990).

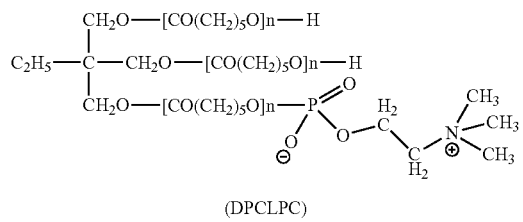

(DPCLPC)

Predried polycaprolactone-300 (17.98 g, 0.0599 mol), triethylamine (6.049 g, 0.0599 mol) and dry THF (150 ml) were placed in a 500 ml three-neck round bottom flask fitted with suba seal, dropping funnel and nitrogen inlet. The solution was cooled to −30° C. and 8.5363 g (0.0599 mol) 2-chloro-2-oxo-1,3,2-dioxaphospholane (COP) dissolved in small amount THF was added slowly via syringe to the solution. The temperature of the reaction was maintained at −30° C. during addition (about 1 hour) and maintained that temperature for two more hours. The reaction mixture was slowly warmed to 10° C. and filtered carefully using a Buchner funnel under reduced pressure. The filtrate was evaporated under reduced pressure to yield a clear viscous liquid. Yield of 2-(2-oxo-1,3,2-dioxaphospholoxy)polycaprolactone diol was 23.74 g.

2-(2-oxo-1,3,2-dioxaphospholoxy)polycaprolactone diol (23.74 g, 0.0537 mol) was placed in a 250 ml glass-pressure bottle with dry acetonitrile (135 mL). The glass bottle was cooled to −30° C. and anhydrous trimethylamine (3.54 mL) was rapidly added to the solution and the pressure bottle was closed and heated to 55° C. with stirring for 3 days. The product was transferred to 100 mL round bottom flask under nitrogen and dried under reduced pressure to yield a slight yellow viscous product. Yield 29 g. The IR and $^1$H NMR confirmed the structure of dihydroxypolycaprolactone phosphoryl choline (DPCLPC).

Dihydroxyglycerol phosphoryl choline (DGPC) was prepared according to the literature reported method (Polym. J. 22, 5, 355-360, 1990, and Australian Journal of Chemistry, 55, 629-634, 2002.

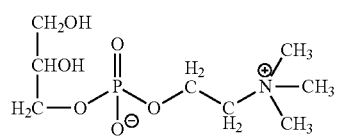

In this case, hydroxyl groups were protected before introducing phosphorylcholine arms using the above described method and subsequently deprotected to yield dihydroxyglycerol phosphoryl choline (DGPC).

Example 21

Materials:
Prepolymer of MLDI and pentaerythritol was prepared according to Example 1. Polycaprolactone triol (MW 300, PCLT-300, Aldrich) was dried by heating under vacuum (0.1 torr) at 90° C. for three hours. Dihydroxypolycaprolactone phosphoryl choline (DPCLPC) was prepared according to the method described in Example 20.

Degassed prepolymer (1.24 g) of Pentaerythritol with MLDI prepared in Example 1 was weighed in to a cavity (20×20×10 mm) made in a Teflon block. Degassed and dried polycaprolactone triol (MW 300, 0.353 g) and DPCLPC (MW 501.4, 0.252 g) was added to this prepolymer followed by water (0.0045 g). The mixture was stirred for a few seconds and then stannous 2-ethyl hexanoate catalyst (0.1-wt % based on total weight of prepolymer, DPCLPC, PCLT and water) was added and stirred further for 5 min. The viscous polymer was then taken into a 2.5 ml syringe and dispensed 0.24 g into each cylindrical cavity (6 mm D×12 mm H) in a multi-cavity Teflon mould and cured overnight at 38° C. to give porous cylindrical polymer test specimens.

The cured polymer samples were tested using Instron (Model 5568) for compressive strength and modulus according to ASTM method F451-95.

The average compressive strength and modulus of the polymer were 9.4±1.6 MPa and 390±1 MPa, respectively.

Example 22

Materials:
Prepolymer of MLDI and D-glucose was prepared according to example 3. Prepolymer was degassed under vacuum (0.1 torr) at 50° C. for 20 minutes under stirring dihydroxypolycaprolactone phosphoryl choline (DPCLPC) was prepared was prepared according to the method described in Example 15. DPCLPC was dried and degassed by heating under vacuum (0.1 torr) at (90° C.) for three hours.

Degassed prepolymer (2.50 g) of D-Glucose with MLDI prepared in Example 3 was weighed in to a cavity (2×2×1 cm) made in a Teflon block. Degassed and dried DPCLPC (MW 501.4, 2.52 g) was added to this prepolymer. The mixture was stirred for a few seconds and then 0.1 wt % of stannous 2-ethyl hexanoate catalyst (0.005 g) was added. Gelatine beads (0.3 mL in water, 100-200 micron size) was added to this mixture and stirred for about 1 minute. The viscous polymer was then taken into a 2.5 ml syringe and dispensed (0.29 g) into each cylindrical cavity (6 mm D×12 mm H) in a multi-cavity Teflon mould and cured overnight at 38° C. to give porous cylindrical polymer test specimens.

The cured polymer samples were tested using Instron (Model 5568) for compressive strength and modulus according to ASTM method F451-95.

The average compressive strength and modulus of the polymer were 0.05±0.1 MPa and 0.18±0.03 MPa, respectively.

Example 23

Materials:
Prepolymer of MLDI and D-glucose was prepared according to example 3. Polycaprolactone triol (MW 300, PCLT-300, Aldrich) was dried by heating under vacuum (0.1 torr) at 90° C. for three hours. Prepolymer was degassed under vacuum (0.1 torr) at 50° C. for 20 min while stirring. Dihydroxypolycaprolactone phosphoryl choline (DPCLPC) was prepared according to the method described in Example 15.

Degassed prepolymer (2.50 g) of D-Glucose with MLDI prepared in Example 3 was weighed in to a cavity (20×20×10 cm) made in a Teflon block. Degassed and dried polycaprolactone triol (MW 300, 0.906 g) and DPCLPC (MW 501.4, 0.252 g) was added to the prepolymer. The mixture was manually stirred using a spatula for few seconds and then stannous 2-ethyl hexanoate catalyst (0.0036 g) was added and stirred for 20 min. Gelatine (0.3 mL, ave. size 100-200 micron, in water) was added to this mixture and stirred for about 1 minute. The viscous polymer was then taken into a 2.5 ml syringe and dispensed 0.29 g into each cylindrical cavity (6 mm D×12 mm H) in a multi-cavity Teflon mould and cured overnight at 38° C. to give porous cylindrical polymer test specimens.

The cured polymer samples were tested using Instron (Model 5568) for compressive strength and modulus according to ASTM method F451-95.

The compressive strength of the polymer was 0.3±0.2 MPa and compressive modulus of 2.9±0.9 MPa.

Example 24

Materials:
Prepolymer of MLDI and D-glucose was prepared according to example 3. Polycaprolactone triol (MW 300, PCLT-300, Aldrich) was dried by heating under vacuum (0.1 torr) at 90° C. for three hours.

1,2-Dihydroxy-N,N-dimethylaminopropane sulfonate (DDAPS) zwitterion was prepared using a procedure adopted from a method previously reported (Ref: Industrial and Engineering Chemistry, Vol 56, 41-45, Fischer, 1954).

The following is a brief description of the method used.

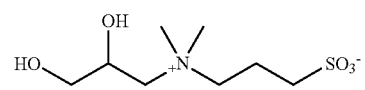

Propane diol (9.88 g, 0.082 mol) was weighed into a three neck flask equipped with a drying tube and nitrogen inlet. Methanol (20 ml) added to this under nitrogen and stirred until dissolved. 1,3-propane sultone (10.1 g, 0.082 mol) was added slowly with stirring at room temperature. The reaction was stirred for about 2 h, until DDAPS zwitterion precipitates out. The zwitterion was filtered and washed with cold methanol and dried under vacuum at 70° C. to yield an amorphous powder. The $^1$H NMR supported the structure of 1,2-dihydroxy-N,N-dimethylamino-propane sulfonate. Yield 12.57 g.

Degassed prepolymer (2.06 g) of D-Glucose with MLDI prepared in Example 3 was weighed in to a cavity (20×20×10 cm) made in a Teflon block. Degassed and dried polycaprolactone triol (MW 300, 0.66 g) and DDAPS (MW 241.16, 0.1 g) was added to the prepolymer followed by water (0.007 g). The mixture was stirred for few seconds and then stannous 2-ethyl hexanoate catalyst (0.0028 g) based was added and stirred for few minutes. The viscous polymer was then taken into a 2.5 ml syringe and dispensed (0.29 g) into each cylindrical cavity (6 mm D×12 mm L) in a multi-cavity Teflon mould and cured overnight at 38° C. to give porous cylindrical polymer test specimens.

The cured polymer samples were tested using Instron (Model 5568) for compressive strength and modulus according to ASTM method F451-95.

The compressive strength of the polymer was 7.1±0.8 MPa and compressive modulus of 80.2±14 MPa.

Example 25

The prepolymer prepared in examples 1, 2 and 3 and the cured polymers made by mixing prepolymer 1 with polycaprolactone triol, EG:lactide and hydroxyapatite as illustrated in examples 11, 12, 13 and 16, respectively were evaluated for their cytotoxicity against human and rat stem cells. The test protocol described in International Organisation for Standardisation Guidelines as stated in ISO 10993-5 (Biological evaluation of medical devices) was used.

Tests for cytotoxicity to determine the biological response of mammalian cells in vitro were developed to look at a) extracts of the device, b) in contact with the device.

Cells used were stem cells from either human and rat origin.

In most cases a negative and positive control for cytotoxicity and a reagent control were used. Culture vessels were of tissue culture grade (TCP), thus providing a good –ve cytotoxic control. Cells were used at 80% confluence to ensure cells were in logarithmic growth phase. Cells were maintained in test conditions overnight (24 hrs) at 37° C. before measuring cytotoxicity with a reagent (MTS), which is only converted with metabolically active cells.

Liquid monomers/prepolymers were tested on pre-seeded cells, added with a culture medium change, and left on cells for 24 hrs, before removing culture medium and adding MTS reagent, incubating for a further 4 hours then reading the absorbance on a plate reader. Solid samples were tested by 1) soaking polymers overnight in culture medium and the next day removing this medium and using it to set up cells in a new TC plate, to look for toxic leachables from the samples and 2) seeding cells directly onto the polymer samples. Cells were tested for cytotoxicity after 24 h as described above.

In all cases, culture medium containing serum was used.

Results were recorded as % Attachment, calculated by result of sample/result of negative cytotoxic control and expressed as a percentage. Results are summarized in Table 1

TABLE 1

Prepolymer cytotoxicity results

| Prepolymer Examples | % Cell attachment | |
|---|---|---|
| | Human stem cells | Human Chondrocytes |
| Example 1 | 80 | 80 |
| Example 2 | 70 | |
| Example 3 | 60 | 100 |
| Example 24 | 100 | 100 |
| Example 10 | 100 | 100 |
| Control | 100 | 100 |

TABLE 2

Polymer cytotoxicity results

| Polymer examples | % Cell attachment | |
|---|---|---|
| | Human stem cells | Rat stem cells |
| Example 11 | 100 | 95 |
| Example 19 | 80 | |
| Example 12 | 90 | — |
| Example 14 | 100 | 95 |
| Example 17 | 70 | 95 |
| Control | 100 | 100 |

Example 26

The in-vitro degradation under hydrolytic and oxidative environments were assessed according to procedures described in Biomaterials Vol. 17, No. 22, 2127, 1996 and Journal of Biomedical Material Research 29, 467-475, 1995, respectively. Following is a brief description of the procedures used.

Polymers prepared in Examples 11, 13, 14, 17, 22, and 23 were used in this study.

Hydrolytic Degradation:

Three porous cylinder specimens of (6 D×12 mm H) (n=3) were placed in a perforated Teflon cage and placed inside a 500 mL Schott bottle containing approximately 400 mL buffered saline solution. Phosphate buffered saline solution of pH 7.4 was used. Schott bottles were stored at 70° C. in an oven and solution pH measurements were taken at different time intervals. pH change in a control solution (without polymer samples) was also measured. Specimens were removed from the buffer and washed with deionised water thoroughly and dried under nitrogen atmosphere for 24 h at 40° C. followed by drying under vacuum (0.1 torr) for 48 h at 40° C. The dry weight was recorded and compared with their initial weight and total weight loss was measured.

Oxidative Degradation:

Three porous cylindrical test specimens (6 D×12 H mm) (n=3) were placed in a perforated Teflon cage and immersed in 400 ml of hydrogen peroxide solution (30% w/v) containing 0.1 molar $CoCl_2$ (pH 3.69) in Schott bottle. Schott bottles were placed in an oven at 70° C. and pH measured at different time intervals. Peroxide solution was replaced with fresh solution after seven days. Change in pH in a control solution (no test specimens) was also measured. Specimens were removed from the peroxide solution and washed with deionised water thoroughly and dried under nitrogen atmosphere for 24 h at 40° C. followed by drying under vacuum (0.1 torr) for 48 h at 40° C. The dry weight was recorded and compared with their initial weight and total wt loss measured.

PBS buffer solution/pH 7.4/70° C. (1 month) and Oxidative environment $CoCl_2/H_2O_2/pH/3.69/70°$ C. (15 days)

TABLE 3

Weight loss due to hydrolytic and oxidative degradation

| Polymer Examples | Wt Loss % in PBS (hydrolytic degradation) One month | Wt loss % in $CoCl_2$ (oxidative degradation) 15 Days |
|---|---|---|
| Example 11 | 7 | 55 |
| Example 17 | 12 | 100 |
| Example 13 | 23 | 100 |
| Example 14 | — | 16 |

TABLE 3-continued

Weight loss due to hydrolytic and oxidative degradation

| Polymer Examples | Wt Loss % in PBS (hydrolytic degradation) One month | Wt loss % in CoCl$_2$ (oxidative degradation) 15 Days |
|---|---|---|
| Example 22 | 49 | — |
| Example 23 | 22 | — |

Example 27

Materials:
Prepolymer of MLDI and D-Glucose was prepared according to Example 3. Polycaprolactone triol (MW 300, PCLT-300, Aldrich) was dried by heating under vacuum (0.1 torr) at 90° C. for three hours and sodium chloride (+80 mesh) (Aldrich) was used a received.

Degassed prepolymer (1.85 g) prepared in Example 3 was weighed in to a cavity (20×20×10 mm) made in a Teflon block. Degassed and dried polycaprolactone triol (MW 300, 0.74 g) was added to this prepolymer followed by 1.77 g of NaCl of approx. mesh size 80. The mixture was manually stirred for few seconds and then stannous 2-ethyl hexanoate catalyst (0.0026, 0.1%) was added and stirred for few minutes. This prepolymer mixture remained a viscous liquid and was taken into a 2.5 ml syringe and dispensed 0.29 g to each of the cylindrical (6 D×12 H mm size) cavities in a Teflon mould and cured overnight at 38° C. The cured polymer was then placed in large excess of deionised water. SEM micrograph showed porosity between 200 and 300 microns.

Example 28

Materials:
Prepolymer of MLDI and D-Glucose was prepared according to Example 3. Polycaprolactone triol (MW 300, PCLT-300, Aldrich) was dried by heating under vacuum (0.1 torr) at 90° C. for three hours and L-ysine (Aldrich) was used as received.

Degassed prepolymer (1.6 g) prepared in Example 3 was weighed in to a cavity (20×20×10 mm) made in a Teflon block. Degassed and dried polycaprolactone triol (MW 300, 0.51 g) was added to this prepolymer followed by L-Llysine (0.047 g) and water (0.006 g). The mixture was stirred for few seconds and then stannous 2-ethyl hexanoate catalyst (0.002, 0.1%) was added and stirred further for 5 min. This prepolymer mixture remained a viscous liquid and was taken into a 2.5 mL syringe and dispensed 0.29 g to each of the cylindrical (6 D×12 H mm size) cavities in a Teflon mould and cured overnight at 38° C. to give porous cylindrical test specimens. The cured polymer samples were tested using Instron (Model 5568 for compressive strength and modulus according to ASTM method F451-95

The average compressive strength and modulus were 26.5±5 MPa and 707±91 MPa, respectively.

Example 29

Materials:
Prepolymer of MLDI and D-Glucose was prepared according to Example 9 Polycaprolactone triol (MW 300, PCLT-300, Aldrich) was dried by heating under vacuum (0.1 torr) at 90° C. for three hours.

Degassed prepolymer (1.38 g) prepared in Example 3 was weighed in to a cavity (20×20×10 mm) made in a Teflon block. Degassed and dried polycaprolactone triol (MW 300, 0.50 g) was added to this prepolymer followed by water (0.005 g). The mixture was stirred for 5 min. This prepolymer mixture remained a viscous liquid and was taken into a 2.5 mL syringe and dispensed 0.29 g to each of the cylindrical (6 D×12 H mm size) cavities in a Teflon mould and cured 72 h at 38° C. to give porous cylindrical test specimens. The cured polymer samples were tested using Instron (Model 5568) for compressive strength and modulus according to ASTM method F451-95.

The average compressive strength and modulus were 30±4 MPa and 521±199 MPa, respectively.

Example 30

Materials:
Prepolymer of MLDI and Pentaerythritol tetrakis (3-mercaptopropionate) (PETPM) was prepared according to Example 10. Polycaprolactone triol (MW 300, PCLT-300, Aldrich) was dried by heating under vacuum (0.1 torr) at 90° C. for three hours.

Degassed prepolymer (1.81 g) prepared in Example 10 was weighed in to a cavity (20×20×10 mm) made in a Teflon block. Degassed and dried polycaprolactone triol (MW 300, 0.48 g) was added to this prepolymer followed by water (0.0048 g). The mixture was manually stirred for few seconds and then stannous 2-ethyl hexanoate catalyst (0.0023, 0.1%) was added and stirred for 5 min. This prepolymer mixture remained a viscous liquid and was taken into a 2.5 mL syringe and dispensed 0.29 g to each of the cylindrical (6 D×12 H mm size) cavities in a Teflon mould and cured overnight at 38° C. to give porous cylindrical test specimens. The cured polymer samples were tested using Instron (Model 5568) for compressive strength and modulus according to ASTM method F451-95.

The average compressive strength and modulus were 20.2±3 MPa and 507±156 MPa, respectively.

Example 31

This example illustrates that human mesenchymal (bone marrow) stem cells can be incorporated with the injectable biodegradable, biocompatible polyurethane/urea compositions of this invention and cured to from solid porous scaffolds without compromising cell viability. In addition cell culture of these plugs show that the stem cells can form new tissue matrix and with appropriate medium can differentiate into osteoblast-like cells.

The injectable polymer system used in this experiment was based on prepolymer prepared according to Example 1, and polycaprolactone triol (MW 300) dried as described in Example 11.

Hollow fibres were precoated with fibronectin (10 μg/ml) at room temp for 2 hrs before seeding with cells (2×10$^6$ cells in 500 μl filled 2 cartridges). Cartridges containing fibres were then placed in 10 cm dishes containing culture media (M199)+10% FCS. Medium was changed twice weekly for 1 week. Cartridges were dismantled, and the fibres were cut into approx 1 mm segments. The cell-seeded hollow fibre tubes were bisected and mixed with the polymer composition described in Example 11, then injected into a rubber tube and allowed to cure for 4 hrs. The polymer plugs containing the cell/hollow fibres were removed from the tube, cut in half and placed into 24 well tissue culture plates. One half of the plug was maintained in standard medium M199+10% FCS, the other half was further supplemented with differentiation medium containing β-glycerol phosphate (1.5 mg/ml), dexamethasone (40 ng/ml) and ascorbate (20 µg/ml) to promote osteoblast differentiation. Cultures were maintained for up to 6 weeks with medium changes every 2-3 days. The polymer plugs were harvested at 6 weeks and samples were processed and stained with standard haematoxylin & eosin, light green, Schiff's reagent, as well as with von Kossa reagent for detection of bone mineralisation.

These experiments revealed the presence of both differentiated (osteoblast-like) and undifferentiated stem cells in the fibre/polymer composite after culture. The differentiated cells showed the presence of bone mineral as evidence by the brown/black Von Kossa staining. These results provide evidence that the cells survive the polymer curing process and can differentiate producing bone mineral.

Example 32

This example illustrates that human chondrocytes can be incorporated with the injectable biodegradable, biocompatible polyurethane/urea compositions of this invention and cured to from solid porous scaffolds without compromising cell viability. In addition cell culture of these plugs show that chondrocytes form new tissue matrix.

The injectable biodegradable, biocompatible polyurethane/urea composition used in this experiment was based on prepolymer prepared according to example 3 and polycaprolactone triol (MW 300).

Human chondrocytes were isolated from fresh cartilage tissue according to Example 1 of PCT WO 02/062357 A1. Fresh cartilage tissue is collected in DMEM/10% FBS or autologous serum containing 100 µg/ml penicillin and streptomycin. After weighing, the tissue is placed in a sterile petri dish containing 3-4 mL of DMEM and dissected into 1 mm$^3$ pieces using a sharp sterile scalpel. It is then digested with 10% w/v trypsin in PBS at 37° C. for 1 hour. Approximately 2 mL of 10% w/v trypsin is used per gram of tissue. The residual tissue pieces are collected by centrifugation (1000 rpm, 5 mins) and washed with PBS, then water (using approximately 5-10 ml per gram of tissue). A second digestion step is then performed overnight at 37° C. using 2 ml of a mixture of bacterial collagenase and hyaluronidase per gram of tissue. The digestion mixture is prepared by adding 2 mg hyaluronidase (1520 units) and 200 µl of collagenase stock (taken from a 3000 unit/ml stock, stored at −70° C. in a buffer of 50 mM tris, 10 mM $CaCl_2$, pH 7.0) to 2 ml of DMEM and filter sterilising. The digested tissue is passed through a 70 µm Nylon cell strainer and the cells are washed and collected by centrifugation. Cell numbers and viability are assessed using a trypan blue count on a small known aliquot.

Gelatin beads were prepared according to Example 7 of PCT WO 02/062357 A1. Gelatin microparticles are synthesized by using emulsion method. Briefly, gelatin is dissolved in 50 mM acetic acid to 20% (w/v). Two hundred milliliters olive oil is warmed up to 37° C. The warmed olive oil is stirred at 300 rpm. Forty milliliters gelatin solution kept at 37° C. is then applied to olive oil through a 20-gauge needle. This solution is also prepared containing 10% w/w native collagen. The emulsion is kept stirred for 90 minutes. The emulsion is then cooled down by stirring at 4° C. for 30 minutes in order to harden the gelatin particles. Five hundred milliliters of 0.2% Triton X-100 in PBS is added to the emulsion and stirred at room temperature for 10 minutes. The mixture is then put in a separating funnel and settled for one hour. The liquid in the lower potion is collected and after gelatin microparticles precipitate, the upper liquid decanted off carefully and the particles rinsed with water two times. Five hundred milliliters of 0.1% glutaraldehyde in PBS is added to the gelatin microparticles and stirred for one hour for cross-linking. The cross-linked gelatin beads are then rinsed with water several times and soaked in ethanol. The ethanol is decanted and the gelatin microparticles dried under vacuum. Before seeding cells, the gelatin beads are rehydrated with PBS overnight and then with chondrocyte medium. The average size of gelatin microparticles is about 110 µm.

Isolated chondrocytes were seeded on gelatin beads according to Example 8 of PCT WO 02/062357 A1. Gelatin beads, providing a surface area of 250-500 cm$^2$, are prewashed with 50 mL of warmed media (DMEM/10% FBS or autologous serum containing 100 µg/ml penicillin and streptomycin) at 37° C. then placed inside a 125 ml spinner bottle. $1\times10^5$ cells, either freshly isolated cells, previously passaged cells or previously isolated and frozen cells, are added to the beads or particles. The bottle is then stirred in a 37° C. incubator (with 5% $CO_2$), at 25 rpm intermittently for 2 minutes every 30 minutes for 3 hours, then 45 rpm intermittently for 2 minutes every 30 minutes for the next 3 hours, then continuously first at 45 rpm for 15 minutes, then 50 rpm for 15 minutes, 55 rpm for 15 minutes, then to the final speed of 60 rpm. The cells are then grown at this speed until 90% confluence is achieved, usually 5-8 days depending on the original inoculum.

For collection of the cells 6 mL of warm 0.3% w/v trypsin is added directly to the washed cells on beads and incubated at 37° C. for 20 minutes. The gelatin beads were digested by the enzyme, releasing the cells into solution without the need for extensive mechanical agitation. Cells were collected by centrifugation at 1000 rpm for 5 mins. Remove the supernatant and gently resuspend the cells in 5 mL of media. Cells are counted using a trypan blue method and re-seeded onto fresh 0.025% cross-linked gelatin beads as previously described at various cell densities for mixture with synthetic delivery polymers.

Prepolymer prepared according to Example 3 (1.00 g) and polycaprolactone triol (MW 300) (0.402 g) were weighed separately into 1 mL syringes and sterilized by gamma radiation (25 KG). Prepolymers in syringes were completely emptied into sterile pots and mixed at ambient temperature for three minutes. The mixture was allowed to stand at ambient temperature in the biohazard safety cabinet. The polymer mixture was allowed to cure for varying times (14 to 80 minutes) in pots until the viscosity began to increase sufficiently to indicate significant curing had occurred. In the example shown the viscosity increased at 63 minutes. Harvested cells on gelatines beads were centrifuged to minimise the amount of medium and then added. Cells/beads (0.25 ml) and polymer were mixed for 1 minute to give a 15% bead/cells to polymer mixture ratio. The total mixture of cell/beads and polymer were transferred as viscous drips into 24 well tissue culture containers. Curing was allowed to continue for a further 2 hrs and 25 minutes to form solid plugs. Culture medium (DMEM/10% FCS) was added and plugs were cultured and examined at various times points ranging from 6 days to 9 weeks. Medium was changed every 2-3 day and samples of tissue plugs were harvested for standard haematoxylin & eosin staining and alcian blue staining.

These experiments demonstrated that human chondrocytes grown and seeded onto beads (gelatin) survive the polymer curing process and can further produce new matrix.

Example 33

Materials:
Pentaerythritol (Aldrich) was dried overnight in a vacuum oven (0.1 torr) at 80° C. MLDI and 1,4-diazabicyclo[2.2.2]octane (DABCO 8154, Air Products & Chemicals Inc) were used as received.

Predried pentaerythritol (5.0 g) was weighed in to a dry three-neck round bottom flask equipped with a magnetic stirrer, nitrogen inlet and drying tube. Methyl 2,6-diisocynato hexanoate (MLDI) (31.17 g) was then weighed and added to the flask followed by DABCO 8154 Catalyst (0.1 wt %). The reaction mixture was stirred and heated at 50° C. for 4 d under nitrogen atmosphere. The homogenous polymer mixture was then degassed under vacuum (0.1 torr) at the above temperature, transferred to a vial under nitrogen atmosphere and stored in the refrigerator. The prepolymer was analysed by GPC and Rheometer (CSR-10) using methods described in Example 1.

The prepolymer number average molecular weight was 1579 and the polydispersity was 1.66. Instantaneous viscosity was $1.0 \times 10^5$ cSt at 23° C.

Example 34

This example illustrates that porous polymers prepared according to this invention are biocompatible. The biocompatibility was evaluated by implanting porous polymer test specimens in Rats for two months.

The porous polymers used in the implant study were prepared by mixing prepolymer A with Component B and the details of various compositions are shown in Table 4. Porous polymer cylinders.

TABLE 4

Composition of polymers used in the rat implant study

| Implant Sample # | Prepolymer A (quantity g) | Component B (quantity g) |
|---|---|---|
| 1 | Example 3 (2.14) | PCLT 300 (0.862) |
| 2 | Example 3 (2.13) | PCLT-300:DDAPS* (0.772:0.103) |
| 3 | Example 3 (1.36) | PCLT-900 (1.64) |
| 4 | Example 5 (2.2) | PCLT-300 (0.9) |
| 5 | Example 3 (2.0) | PCLT-300:DPCLPC** (0.48:0.808) |
| 6 | Example 3 (2.0 g) | PCLT-300:DPCLPC** (0.725:0.201) |

*DDAPS was prepared according to the procedure in Example 24
**DPCLPC was prepared according to the procedure in Example 20

Cylindrical test specimens (6 D×10 H mm) were prepared using the following procedure for all implant samples.

Degassed prepolymer was weighed in to a cavity (20×20×10 cm) made in a Teflon block. Degassed and dried prepolymer B was weighed and added to the prepolymer A. The mixture was stirred for few seconds and then stannous 2-ethyl hexanoate catalyst (0.25% of total mixture) was added and stirred for 20 min. Gelatine beads (ave. size 100-200 micron, in water, 0.1 mL per 1.0 g prepolymer mixture) was added to this mixture and stirred for about 1 minute. The viscous polymer was then taken into a 2.5 mL syringe and dispensed 0.29 g into each cylindrical cavity (6 mm D×10 mm H) in a multi-cavity Teflon mould and cured overnight at 38° C. to give porous cylindrical polymer test specimens.

Implantation Procedure and Results:

The in vivo biocompatibility and biodegradation of pre-formed polymers were conducted using standard methods in female rats. The procedure is as follows: Eight week old, female, Sprague Dawley rats were anaesthetised using a ketamine/xylazine mixture. Once anaesthetised a subcutaneous pocket was created in the back of the rat. Two 6 mm D×10 mm H sterile preformed polymers were inserted into the pocket, one to the left and the other to the right of the initial incision. Once in place the wound was closed with a 9 mm wound clip. Animals were monitored every 2 hrs for the first 6 hours and every 12 hours for the first 3 days. Intensive monitoring was undertaken every 2 weeks, which included weighing the animals, visual monitoring of the surgical site, and measuring of the polymers with digital callipers (length and width) to assess degradation.

At set time points the animals were killed with Nembutal (sodium pentobarbitone), serum was collected, polymer with surrounding tissue was excised. The polymer was fixed in formalin and processed for histological analysis. All major organs prior to removal were assessed for signs of gross pathology. Once removed, these organs were weighed and then pieces processed for histology.

After 2 and 4 months in vivo all rats showed no signs of disease, all gained weight similar to the controls and there was no swelling or adverse reactions to the presence of the polymers. No gross pathology was seen in any major organ. After 4 months a small soft capsule had formed around the polymers. No calcification was noted. Analysis of Haematoxylin and Eosin stained sections at 2 and 4 months revealed a normal looking dermis. Occasional neutrophils were noted however there presence was due to mechanical shearing induced by some movement of polymer. At 2 months some polymers had fibroblast infiltration of polymer pores that were adjacent to the dermal tissue. This became more pronounced at 4 months. At 4 months the fibroblast infiltration had progressed further into the polymer than just on the edge. FIG. 18 shows histology images illustrating good tissue integration after two-month implantation.

Example 35

Materials:

Prepolymer of MLDI and D-glucose was prepared according to Example 3. Polycaprolactone triol (MW 300, Aldrich) was dried by heating under vacuum (0.1 torr) at 90° C. for three hours and 2-(2-aminoethylamino)ethanol (Aldrich) was used as received.

Degassed prepolymer (1.35 g) prepared in Example 3 was weighed in to a cavity (20×20×10 mm) made in a Teflon block. Degassed and dried polycaprolactone triol (0.438 g) and water (0.005 g) were added. The mixture was manually stirred for several minutes and then 2-(2-aminoethylamino) ethanol (0.014 g) was added and stirred for additional 1 min. This prepolymer mixture remained a viscous liquid and was taken into a 2.5 mL syringe and dispensed 0.29 g to each of the cylindrical (6 mm D×12 mm H) cavities in a Teflon mould and cured overnight at 38° C. to give porous cylindrical test specimens. The cured polymer samples were tested using Instron (Model 5568) according to ASTM method F451-95.

The average compressive strength and modulus were 18.4±4 MPa and 691±104 MPa, respectively.

Example 36

Materials:

Prepolymer of MLDI and D-glucose was prepared according to Example 3. Four-arm amine terminated PAMAM dendrimer (generation 0) was purchased from Aldrich as a 20 wt. % solution in methyl alcohol. PAMAM in PBS buffer solution was prepared by evaporating methanol and dissolving to make a 20 mg/mL dendrimer in 0.0104 molar PBS buffer solution.

Degassed prepolymer (1.29 g) prepared in Example 3 was weighed in to a cavity (20×20×10 mm) made in a Teflon block. A solution of PAMAM dendrimer in buffer solution (MW 516.68, 0.5 g) was added to this prepolymer. The mixture was stirred for few seconds before taking into a 2.5 ml syringe and dispensed 0.29 g to each of the cylindrical (6

D×12 H mm size) cavities in a Teflon mould and cured overnight at 38° C. and gave solid, porous cylindrical test specimens.

Example 37

Materials:

MLDI and titanium (IV) butoxide were used as received, whereas pentaerythritol (Aldrich) was dried as described in Example 1.

Predried pentaerythritol (2.0 g) was weighed into a dry three-neck round bottom flask equipped with a magnetic stirrer, nitrogen inlet and drying tube. Methyl 2,6-diisocynato hexanoate (MLDI) (12.46 g) was weighed and added to the flask followed by titanium IV butoxide (0.014 g). The reaction mixture was stirred and heated at 50° C. for 24 h under nitrogen atmosphere. The homogenous polymer mixture was then degassed under vacuum (0.1 torr) and transferred to a vial under nitrogen atmosphere and stored in the refrigerator.

The prepolymer number average molecular weight was 1366 and the polydispersity was 1.85. Instantaneous viscosity was $8.0 \times 10^4$ cSt at 23° C.

Degassed prepolymer (1.62 g) prepared was weighed in to a cavity (20×20×10 mm) made in a Teflon block. Degassed and dried polycaprolactone triol (MW 300, 0.595 g) was added to this prepolymer followed by water (0.005 g). The mixture was stirred for few seconds and then catalyst titanium (IV) butoxide (0.002, 0.1%) was added and stirred. This prepolymer mixture remained a viscous liquid and was taken into a 2.5 mL syringe and dispensed 0.29 g to each of the cylindrical (6 mm D×12 mm H) cavities in a Teflon mould and cured overnight at 38° C. to give a porous cylindrical test specimens. The cured polymer samples showed compressive strength and modulus of 21.3±2.9 MPa and 678±57 MPa, respectively when tested using Instron (Model 5568) according to ASTM method F451-95.

Example 38

Materials:

Linear polycaprolactone diol (MW 400, Aldrich) was dried in a vacuum oven (0.1 torr) at 80° C. for 3 h. MLDI and stannous 2-ethyl hexanoate were used as received.

Predried polycaprolactone diol MW 400 (5.0 g) was weighed in to a dry three-neck round bottom flask equipped with a magnetic stirrer, nitrogen inlet and drying tube. Methyl 2,6-diisocynato hexanoate (MLDI) (5.3 g) was then added to the flask followed by 0.1 wt % stannous 2-ethyl hexanoate catalyst. The reaction mixture was stirred and heated at 50° C. for 4 h under nitrogen atmosphere. The homogenous polymer mixture was then degassed under vacuum (0.1 torr) and stored in the refrigerator. The prepolymer was analysed by GPC and showed number average molecular weight 1970 and polydispersity 1.53.

Example 39

Materials:

L-lysine (Aldrich), MLDI and stannous 2-ethyl hexanoate were used as received.

L-lysine (2.03 g) was weighed in to a dry three-neck round bottom flask equipped with a magnetic stirrer, nitrogen inlet and drying tube. Methyl 2,6-diisocynato hexanoate (MLDI) (8.85 g) was added to the flask followed by 0.1 wt % stannous 2-ethyl hexanoate catalyst. The reaction mixture was stirred and heated at 50° C. for 112 h under nitrogen atmosphere. The homogenous polymer mixture was then degassed under vacuum (0.1 torr) at the above temperature and stored in the refrigerator. The prepolymer was analysed by GPC and showed number average molecular weight 620 and the polydispersity 1.25.

Example 40

Materials:

Prepolymer of MLDI and DG-Glucose prepared according to Example 3. Polycaprolactone triol (MW 300, PCLT-300, Aldrich) was dried by heating under vacuum (0.1 torr) at 90° C. for three hours. Peptide JAMR. 49 (Ac-GEKGPAGER-GAXGPAGPRGPXGPXGPXGPXGV-OH (X=Hyp) was used as received (MW 2800).

Degassed prepolymer (1.52 g) prepared in Example 3 was weighed in to a cavity (20×20×10 mm) made in a Teflon block. Degassed and dried polycaprolactone triol (MW 300, 0.543 g) was added to this prepolymer followed by the peptide (0.205 g) and water (0.005 g). The mixture was manually stirred for several minutes and then stannous 2-ethyl hexanoate catalyst (0.002, 0.1%) was added and stirred. This prepolymer mixture remained a viscous liquid and was taken into a 2.5 ml syringe and dispensed 0.29 g to each of the cylindrical (6 mm D×12 mm H) cavities in a Teflon mould and cured overnight at 38° C. to give a porous cylindrical test specimens. The cured polymer samples were tested using Instron (Model 5568) according to ASTM method F451-95 and exhibited 14.2±6.9 MPa compressive strength and 517±195 MPa compressive modulus.

It will be appreciated that the invention is not limited to the core molecules, isocyanates, or functional oligomers and degradable arms as set out hereinabove. Rather the limits of this invention will be appreciated by the functional need to deliver a preferably injectable and flowable prepolymer composition for in vivo or ex vivo low exotherm curing with a functional oligomer so as to form as polymeric, optionally living scaffold. In particular, however, an injectable biodegradable, biocompatible polyurethane/urea composition must meet the following requirements to be useful in bone and cartilage applications. Ideally the prepolymer should be in liquid/paste form, sterilizable without causing any chemical change, and have the capacity to incorporate biological matrix components. Upon injection the prepolymer mixture should bond to biological surface and cures to a solid and preferably porous scaffold with appropriate mechanical properties to suit the application. The curing should be with minimal heat generation and the chemical reactions involved in curing should not damage the cells or adjacent tissues. The cured polymer while facilitating cell in-growth, proliferation and migration, should ideally be degraded to biocompatible components that are absorbed to the body or released from the body.

REFERENCES

1. Shalaby S W. Bioabsorbable Polymers. Swarbrick J, Boylan J C editors. Encyclopedia of Pharmaceutical Technology 1988; vol 1; p 465-476
2. Hayashi T. Biodegradable polymers for biomedical applications. Prog Polym Sci 1994; 19; p 663-702.
3. Holland S J, Tighe B J. Biodegradable polymers. Advances in Pharmaceutical Science, vol 6, London: Academic Press; 1992; p 101-164.
4. Middleton J C, Tipton A J. Synthetic biodegradable polymers as orthopedic devices. Biomaterials 2000; 21; 2335-2346.

5. Behravesh E, Yasko A W, Engle P S, Mikos A G. Synthetic biodegradable polymers for orthopaedic applications. Clinical Orthopaedics and Related Research, Number 367S Lippincott Williams and Wilkins, Inc; 1999. p s118-s185.
6. Temenoff J S, Mikos A G. Injectable biodegradable materials for orthopaedic tissue engineering. Biomaterials 2000; 21; 2405-2412.
7. Agrawal C M, Athanasiou K A, Heckman J D. Biodegradable PLA/PGA polymers for tissue engineering in orthopaedics. Material Science Forum 1997; 250; 115-128.
8. Mikos A G, Temenoff J S. Formation of highly porous biodegradable scaffolds for tissue engineering. EJB Electron. J Biotechnol 2000; 3(9); no pp. given (available on http://www.ejb.org/content/vol3/issue2/full/5)
9. Muggli D S, Burkoth A K, Keyser S A, Lee H R, Anseth K S. Reaction behaviour of biodegradable, photo-cross linkable polyanhydrides. Macromolecules 1998; 31; 4120-4125.
10. Gunatillake P A, Meijs G F, and McCarthy S J. "Developments in Design and Synthesis of Biostable Polyurethanes", in Biomedical Applications of Polyurethanes Eds Vermette, Griesser, Laroche, Guidoin, Landes Bioscience, 2001 p 160-170.
11. Bruin P, Veenstra G J, Nijenhuis A J, Pennings A J. Design and synthesis of biodegradable poly(ester-urethane) elastomer networks composed of non-toxic building blocks. Makromol. Chem., Rapid Commun. (1988), 9(8), 589-94.
12. Saad B, Casotti M, Huber T H, Schmutz P, Welti M, Uhlschmid G K. Neuenschwander P, Suter U W. In vitro evaluation of the biofunctionality of osteoblasts cultured on DegraPol-foam. J. Biomater. Sci. Polym. Ed. (2000), 11(8), 787-800.
13. Saad B, Moro M, Tun-Kyi A, Welti M, Schmutz P, Uhlschmid G K, Neuenschwander P, Suter U W. Chondrocyte biocompatibility of DegraPol foam: in vitro evaluations. J. Biomater. Sci., Polym. Ed. (1999), 10(11), 1107-1119.
14. Bennett S L, Jiang Y, Gruskin E A., Connolly K M U.S. Pat. No. 6,207,767 B1 (1997)
15. Zhang, Jian Ying; Beckman, Eric J.; Piesco, Nicholas P.; Agarwal, Sudha. Department of Chemical & Petroleum Engineering, University of Pittsburgh, Pittsburgh, Pa., USA. Biomaterials (2000), 21(12), 1247-1258.
16. Storey, R. F.; Wiggins, J. S.; Puckett, A. D. Dep. Polymer Sci., Univ. Southern Mississippi, Hattiesburg, Miss., USA. J. Polym. Sci., Part A: Polym. Chem. (1994), 32(12), 2345-63.
17. Storey, Robson F.; Hickey, Timothy P. Dep. Polym. Sci., Univ. S. Mississippi, Hattiesburg, Miss., USA. Polymer (1994), 35(4), 830-8.
18. Wiggins, Jeffrey S.; Storey, Robson F. Dep. Polym. Sci., Univ. South. Mississippi, Hattiesburg, Miss., USA. Polym. Prepr. (Am. Chem. Soc., Div. Polym. Chem.) (1992), 33(2), 516-17.
19. Storey, R. F.; Wiggins, J. S. Dep. Polym. Sci., Univ. South. Mississippi, Hattiesburg, Miss., USA. Annu. Tech. Conf.—Soc. Plast. Eng. (1992), 50th (Vol. 1), 734-7.
20. Bruin, P.; Smedinga, J.; Pennings, A. J.; Jonkman, M. F. Dep. Polym. Chem., Univ. Groningen, Groningen, Neth. Biomaterials (1990), 11(4), 291-5.
21. Spaans, Coenraad Jan; Rienstra, Onno; Pennings, Albert Johan; Hermina de Groot, Jacqueline. (Polyganics B.V., Neth.). Eur. Pat. Appl. (2001), 12 pp, EP 1138336 A1 20011004
22. Spaans, C. J.; Belgraver, V. W.; Rienstra, O.; de Groot, J. H.; Veth, R. P. H.; Pennings, A. J. Biomaterials (2000), 21(23), 2453-2460.
23. Spaans, Coenraad J.; De Groot, Jacqueline H.; Dekens, Folkert G.; Veth, Rene P. H.; Pennings, Albert J. Department of Polymer Chemistry, Polym. Prepr. (Am. Chem. Soc., Div. Polym. Chem.) (1999), 40(2), 589-590.
24. van Tienen, Tony G.; Heijkants, Ralf G. J. C.; Buma, Pieter; de Groot, Jacqueline H.; Pennings, Albert J.; Veth, Rene P. H. Biomaterials (2002), 23(8), 1731-1738.
Woodhouse K M, Skarja G A U.S. Pat. No. 6,221,997 B1

The invention claimed is:

1. A biodegradable, biocompatible polyurethane/urea polymer composition comprising the reaction product of:
   a) a flowable prepolymer comprising the reaction product of:
      i) one or more isocyanates; and
      ii) one or more multifunctional core molecules having a molecular weight of 400 or less and at least two functional groups that react with said isocyanate thereby forming urethane or urea groups; and
   b) one or more soft segment-forming functional oligomers chosen from:
      i) linear oligomers;
      ii) star oligomers;
      iii) dendrimeric oligomers; and
      iv) hyperbranched oligomers;
   wherein the functional oligomer has degradable arms and is selected from the group consisting of lactides, glycolides, lactide/glycolides, caprolactones, propylene fumarates, glycolic acid, dioxanones, anhydrides and polyorthoesters;
   wherein the flowable prepolymer is curable with the functional oligomer at 30° C.; and
   wherein the polymer composition comprises one or more bioactive moieties.

2. The biodegradable, biocompatible polyurethane/urea polymer composition according to claim 1 wherein the one or more bioactive moieties is chemically bonded to the composition.

3. The biodegradable, biocompatible polyurethane/urea polymer composition according to claim 1 wherein the one or more bioactive moieties is chemically bonded to the composition via one or more hydrolysable linkages.

4. The biodegradable, biocompatible polyurethane/urea polymer composition according to claim 1 wherein the one or more bioactive moieties is chemically bonded to the multifunctional core molecule.

5. The biodegradable, biocompatible polyurethane/urea polymer composition according to claim 4 wherein the multifunctional core molecule has one of the following structures:

$[H]_m$-A-$[B]_n$;

$[H-D]_m$-A-$[E-B]_n$; or $[H-D]_m$-A-$[(E)_p$-B$]_n$ wherein

A is a core molecule sub-structure;

H is an active hydrogen atom;

B is a bioactive moiety which is bound to A via one or more hydrolysable linkages;

D is a degradable arm comprising one or more hydrolysable linkages and which is bound to A via the one or more hydrolysable linkages, said degradable arm being terminated by an active hydrogen atom;

E is a degradable arm comprising one or more hydrolysable linkages and which is bound to A via the one or more hydrolysable linkages, said degradable arm being terminated by a bioactive moiety B via a hydrolysable linkage;

m is an integer of 2 or greater;

n is an integer of 1 or greater; and p is an integer of 1 or greater.

6. The biodegradable, biocompatible polyurethane/urea polymer composition according to claim 1 wherein the one or more bioactive moieties is chemically bonded to the isocyanate.

7. The biodegradable, biocompatible polyurethane/urea polymer composition according to claim 1 wherein the one or more bioactive moieties is chemically bonded to the functional oligomer.

8. The biodegradable, biocompatible polyurethane/urea polymer composition according to claim 1 wherein the bioactive moiety is selected from the group consisting of ascorbic acid, glycerol, glucose, lysine, lactic acid and ethanol.

9. The biodegradable, biocompatible polyurethane/urea polymer composition according to claim 1 wherein the one or more bioactive moieties is hydrolytically releasable from the polymer composition.

10. The biodegradable, biocompatible polyurethane/urea polymer composition according to claim 1 wherein the one or more bioactive moiety is hydrolytically releasable at a rate that is faster than the degradation rate of the biodegradable polymer backbone.

11. A biodegradable, biocompatible polyurethane/urea polymer composition according to claim 1, comprising the reaction product of:
(a) a flowable prepolymer comprising the reaction product of any one of ascorbic acid, glycerol or glucose and diisocyanate, and
(b) a functional oligomer having degradable arms.

12. A biodegradable, biocompatible polyurethane/urea polymer composition according to claim 1 where the bioactive moiety is a phosphorylcholine.

13. A biodegradable, biocompatible polyurethane/urea polymer composition according to claim 1, comprising the reaction product of:
(a) a flowable prepolymer comprising the reaction product of a multifunctional core molecule and diisocyanate, and
(b) the reaction product of polycaprolactone triol and phosphoryl choline.

14. A biodegradable, biocompatible polyurethane/urea polymer composition according to claim 1, comprising the reaction product of:
(a) a flowable prepolymer comprising the reaction product of a multifunctional core molecule and diisocyanate, and
(b) the reaction product of ethylene glycol, lactide and polycaprolactone triol.

15. A biodegradable, biocompatible polyurethane/urea polymer composition according to claim 1, comprising the reaction product of:
(a) a flowable prepolymer comprising the reaction product of a multifunctional core molecule and ethyl 2,6-diisocyanato hexanoate, and
(b) a functional oligomer having degradable arms.

16. The biodegradable, biocompatible polyurethane/urea polymer composition according to claim 1 wherein the one or more bioactive moieties comprises gelatine or hydroxyapatite.

17. A biodegradable, biocompatible polyurethane/urea polymer composition according to claim 1 further comprising one or more chain extenders.

18. A biodegradable, biocompatible polymeric scaffold comprising a cured biocompatible, biodegradable polyurethane/urea composition according to claim 1.

19. A process for the preparation of a biocompatible, biodegradable polyurethane/urea composition according to claim 1, comprising
reacting one or more isocyanates with one or more multifunctional core molecules having a molecular weight less than 400 so as to form a flowable prepolymer having urethane or urea groups; and
reacting said prepolymer with one or more functional oligomers with degradable arms and optionally, appropriate amounts of water and catalyst under conditions such that the reaction temperature does not exceed 90° C.

20. A process according to claim 19 optionally comprising the addition of one or more chain extenders.

21. A method of treatment of damaged bone or cartilage in a patient requiring such treatment, the method comprising administering to said patient a biocompatible, biodegradable polyurethane/urea composition according to claim 1, said administration occurring by the implant of a scaffold formed ex vivo from a cured form of said polyurethane/urea composition, or by the injection of said polymer in an uncured form for in vivo curing and scaffold formation.

22. A process of repairing bone or cartilage comprising integrating the scaffold according to claim 17 with said bone or cartilage.

* * * * *